(12) United States Patent
Ingimundarson et al.

(10) Patent No.: US 10,492,940 B2
(45) Date of Patent: Dec. 3, 2019

(54) ORTHOPEDIC DEVICES UTILIZING ROTARY TENSIONING

(71) Applicant: OSSUR HF, Reykjavik (IS)

(72) Inventors: Arni Thor Ingimundarson, Gardabaer (IS); Palmi Einarsson, Kopavogur (IS); Irving Hu, San Francisco, CA (US); Jane Lee, Fullerton, CA (US)

(73) Assignee: OSSUR HF, Reykjavik (IS)

( * ) Notice: Subject to any disclaimer, the term of this patent is extended or adjusted under 35 U.S.C. 154(b) by 1096 days.

(21) Appl. No.: 14/513,406

(22) Filed: Oct. 14, 2014

(65) Prior Publication Data

US 2015/0032041 A1 Jan. 29, 2015

Related U.S. Application Data

(62) Division of application No. 12/466,597, filed on May 15, 2009, now Pat. No. 8,858,482.

(60) Provisional application No. 61/092,297, filed on Aug. 27, 2008, provisional application No. 61/054,766, filed on May 20, 2008, provisional application No. 61/054,764, filed on May 20, 2008, provisional application No. 61/071,747, filed on May 15, 2008.

(51) Int. Cl.
*A61F 5/01* (2006.01)
*A61F 5/02* (2006.01)
*A61H 3/00* (2006.01)

(52) U.S. Cl.
CPC .......... *A61F 5/0102* (2013.01); *A61F 5/0111* (2013.01); *A61F 5/0123* (2013.01); *A61F 5/022* (2013.01); *A61H 3/00* (2013.01); *A61F 2250/001* (2013.01)

(58) Field of Classification Search
CPC .... A61F 5/0102; A61F 5/0111; A61F 5/0123; A61F 5/022; A61F 5/0195
USPC .... 602/23, 27–30; 36/89, 117.5, 140, 117.8, 36/50.1, 50.5, 110, 117.1, 118.2–118.4, 36/118.8, 118.9; 128/882
See application file for complete search history.

(56) References Cited

U.S. PATENT DOCUMENTS 2,070,093 A 2/1937 Roe
3,793,749 A 2/1974 Gertsch et al.
(Continued)

FOREIGN PATENT DOCUMENTS

CA 2 112 789 A1 8/1994
CA 2 114 387 A1 8/1994
(Continued)

OTHER PUBLICATIONS

"Rollerblade TFS Skate Laces AERO", http://www.inlinewarehouse.com/viewlarge.html?PCODE=TFS, retrieved on Jan. 7, 2010, 1 page.
(Continued)

*Primary Examiner* — Kari K Rodriquez
(74) *Attorney, Agent, or Firm* — Workman Nydegger

(57) ABSTRACT

An orthopedic device has at least one flexible or rigid frame member contoured to generally correspond to an anatomical limb. The device also includes a tightening system having a dial tensioning device and at least one cable and/or strap connected to the dial tensioning device. The dial tensioning device has a rotary ratchet permitting incremental adjustment of the cable and/or strap. Adjustment of the dial tensioner in a first direction secures the frame member to the limb.

8 Claims, 22 Drawing Sheets

(56) References Cited

U.S. PATENT DOCUMENTS

| | | |
|---|---|---|
| 3,808,644 A | 5/1974 | Schoch |
| 3,889,664 A | 6/1975 | Heuser et al. |
| 3,926,182 A | 12/1975 | Stabholz |
| 4,261,081 A | 4/1981 | Lott |
| 4,433,456 A | 2/1984 | Baggio |
| 4,551,932 A | 11/1985 | Schoch |
| 4,555,830 A | 12/1985 | Petrini et al. |
| 4,574,500 A | 3/1986 | Aldinio et al. |
| 4,616,524 A | 10/1986 | Bidoia |
| 4,619,657 A | 10/1986 | Keates et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,741,115 A | 5/1988 | Pozzobon |
| 4,748,726 A | 6/1988 | Schoch |
| 4,760,653 A | 8/1988 | Baggio |
| 4,799,297 A | 1/1989 | Baggio et al. |
| 4,802,291 A | 2/1989 | Sartor |
| 4,811,503 A | 3/1989 | Iwama |
| 4,841,649 A | 6/1989 | Baggio et al. |
| 4,884,760 A | 12/1989 | Baggio et al. |
| 4,961,544 A | 10/1990 | Bidoia |
| 5,042,177 A | 8/1991 | Schoch |
| 5,062,225 A | 11/1991 | Gorza |
| 5,065,481 A | 11/1991 | Walkhoff |
| 5,092,321 A | 3/1992 | Spademan |
| 5,117,567 A | 6/1992 | Berger |
| 5,152,038 A | 10/1992 | Schoch |
| 5,157,813 A | 10/1992 | Carroll |
| 5,177,882 A | 1/1993 | Berger |
| 5,181,331 A | 1/1993 | Berger |
| 5,183,036 A | 2/1993 | Spademan |
| 5,205,055 A * | 4/1993 | Harrell ............ A43B 5/1633 36/50.1 |
| 5,249,377 A | 10/1993 | Walkhoff |
| 5,319,868 A | 6/1994 | Hallenbeck |
| 5,325,613 A | 7/1994 | Sussmann |
| 5,327,662 A | 7/1994 | Hallenbeck |
| 5,365,947 A | 11/1994 | Bonutti |
| 5,433,648 A | 7/1995 | Frydman |
| 5,437,619 A | 8/1995 | Malewicz et al. |
| 5,477,593 A | 12/1995 | Leick |
| 5,502,902 A | 4/1996 | Sussmann |
| 5,599,288 A | 2/1997 | Shirley et al. |
| 5,638,588 A | 6/1997 | Jungkind |
| 5,647,104 A | 7/1997 | James |
| 5,669,116 A | 9/1997 | Jungkind |
| 5,685,830 A | 11/1997 | Bonutti |
| 5,732,483 A | 3/1998 | Cagliari |
| 5,737,854 A | 4/1998 | Sussmann |
| 5,819,378 A | 10/1998 | Doyle |
| 5,848,979 A | 12/1998 | Bonutti et al. |
| 5,891,061 A | 4/1999 | Kaiser |
| 5,934,599 A | 8/1999 | Hammerslag |
| 6,159,248 A | 12/2000 | Gramnas |
| 6,202,953 B1 | 3/2001 | Hammerslag |
| 6,206,932 B1 | 3/2001 | Johnson |
| 6,256,798 B1 | 7/2001 | Egolf et al. |
| 6,267,390 B1 | 7/2001 | Maravetz et al. |
| 6,289,558 B1 | 9/2001 | Hammerslag |
| 6,413,232 B1 | 7/2002 | Townsend et al. |
| 6,416,074 B1 * | 7/2002 | Maravetz ............ A43B 5/0401 280/613 |
| 6,502,577 B1 | 1/2003 | Bonutti |
| 6,503,213 B2 | 1/2003 | Bonutti |
| 6,689,080 B2 | 2/2004 | Castillo |
| 6,711,787 B2 | 3/2004 | Jungkind et al. |
| 6,769,155 B2 | 8/2004 | Hess et al. |
| 6,770,047 B2 | 8/2004 | Bonutti |
| 6,827,653 B2 | 12/2004 | Be |
| 6,921,377 B2 | 7/2005 | Bonutti |
| D519,637 S | 4/2006 | Nordt et al. |
| D520,141 S | 5/2006 | Nordt et al. |
| D521,644 S | 5/2006 | Nordt et al. |
| 7,128,724 B2 | 10/2006 | Marsh |
| 7,134,224 B2 | 11/2006 | Elkington et al. |
| 7,198,610 B2 | 4/2007 | Ingimundarson et al. |
| 7,207,126 B2 | 4/2007 | Gantier |
| 7,235,059 B2 | 6/2007 | Mason et al. |
| 7,281,341 B2 | 10/2007 | Reagan et al. |
| 7,306,573 B2 | 12/2007 | Bonutti |
| 7,331,126 B2 | 2/2008 | Johnson |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,513,018 B2 | 4/2009 | Koenig et al. |
| 7,591,050 B2 | 9/2009 | Hammerslag |
| 7,600,660 B2 | 10/2009 | Kasper et al. |
| 7,617,573 B2 | 11/2009 | Chen |
| 7,618,386 B2 | 11/2009 | Nordt, III et al. |
| 7,618,389 B2 | 11/2009 | Nordt, III et al. |
| 7,670,306 B2 | 3/2010 | Nordt, III et al. |
| 7,699,797 B2 | 4/2010 | Nordt, III et al. |
| 7,704,219 B2 | 4/2010 | Nordt, III et al. |
| 7,806,842 B2 | 10/2010 | Stevenson et al. |
| 7,857,776 B2 | 12/2010 | Frisbie |
| 7,862,621 B2 | 1/2011 | Kloos et al. |
| 7,878,998 B2 | 2/2011 | Nordt, III et al. |
| 7,887,500 B2 | 2/2011 | Nordt, III et al. |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,993,296 B2 | 8/2011 | Nordt, III et al. |
| 8,002,724 B2 | 8/2011 | Hu et al. |
| 8,038,635 B2 | 10/2011 | Dellanno |
| 8,038,637 B2 | 10/2011 | Bonutti |
| 8,091,182 B2 | 1/2012 | Hammerslag et al. |
| 2002/0095750 A1 | 7/2002 | Hammerslag |
| 2003/0093882 A1 | 5/2003 | Gorza et al. |
| 2003/0204938 A1 | 11/2003 | Hammerslag |
| 2005/0081339 A1 | 4/2005 | Sakabayash |
| 2005/0160627 A1 | 7/2005 | Dalgaard et al. |
| 2005/0247813 A1 | 11/2005 | Kovacevich et al. |
| 2005/0273025 A1 | 12/2005 | Houser |
| 2005/0284003 A1 | 12/2005 | Dalgaard et al. |
| 2006/0015980 A1 | 1/2006 | Nordt, III et al. |
| 2006/0015988 A1 | 1/2006 | Philpott et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0156517 A1 | 7/2006 | Hammerslag et al. |
| 2006/0174516 A1 | 8/2006 | Peruzzo |
| 2006/0185357 A1 | 8/2006 | Kovacevich et al. |
| 2006/0200057 A1 * | 9/2006 | Sterling ............ A61F 5/0123 602/5 |
| 2006/0202077 A1 | 9/2006 | Kovacevich et al. |
| 2006/0202078 A1 | 9/2006 | Kovacevich et al. |
| 2007/0039085 A1 | 2/2007 | Kovacevich et al. |
| 2007/0169378 A1 | 7/2007 | Sodeberg et al. |
| 2008/0034459 A1 | 2/2008 | Nordt, III et al. |
| 2008/0039757 A1 | 2/2008 | Nordt, III et al. |
| 2008/0039764 A1 | 2/2008 | Nordt, III et al. |
| 2008/0039765 A1 | 2/2008 | Nordt, III et al. |
| 2008/0039767 A1 | 2/2008 | Nordt, III et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |

(56) References Cited

U.S. PATENT DOCUMENTS

| | | |
|---|---|---|
| 2008/0066345 A1 | 3/2008 | Hammerslag et al. |
| 2008/0066346 A1 | 3/2008 | Hammerslag et al. |
| 2008/0083135 A1 | 4/2008 | Hammerslag et al. |
| 2008/0091132 A1 | 4/2008 | Bonutti |
| 2008/0319362 A1 | 12/2008 | Joseph |
| 2009/0030353 A1 | 1/2009 | Bonutti et al. |
| 2009/0090026 A1 | 4/2009 | Mosher |
| 2009/0287128 A1 | 11/2009 | Ingimundarson et al. |
| 2010/0139057 A1 | 6/2010 | Soderberg et al. |
| 2010/0268139 A1 | 10/2010 | Garth |
| 2010/0274364 A1 | 10/2010 | Pacanowsky et al. |
| 2010/0299959 A1 | 12/2010 | Hammerslag et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0144554 A1 | 6/2011 | Weaver, II et al. |
| 2011/0178448 A1 | 7/2011 | Einarsson |
| 2011/0184326 A1 | 7/2011 | Ingimundarson et al. |
| 2011/0197362 A1 | 8/2011 | Chella et al. |
| 2011/0266384 A1 | 11/2011 | Goodman et al. |
| 2012/0010547 A1 | 1/2012 | Hinds |
| 2012/0029404 A1 | 2/2012 | Weaver, II et al. |

FOREIGN PATENT DOCUMENTS

| | | |
|---|---|---|
| CH | 577 282 A5 | 7/1976 |
| CH | 612 076 A5 | 7/1979 |
| CH | 624 001 A5 | 7/1981 |
| DE | 2 341 658 A1 | 3/1974 |
| DE | 38 22 113 A1 | 1/1990 |
| DE | 93 15 776.2 U1 | 2/1995 |
| DE | 295 03 552.8 U1 | 4/1995 |
| DE | 199 45 045 A1 | 3/2001 |
| DE | 100 57 286 A1 | 5/2002 |
| EP | 0 201 051 A1 | 11/1986 |
| EP | 0 393 380 B1 | 9/1992 |
| EP | 0 589 233 A1 | 3/1994 |
| EP | 0 614 624 A1 | 9/1994 |
| EP | 0 614 625 A1 | 9/1994 |
| EP | 0 589 232 B1 | 11/1995 |
| EP | 0 693 260 B1 | 9/1998 |
| EP | 0 651 954 B1 | 2/1999 |
| EP | 1 236 412 A1 | 9/2002 |
| FR | 2 177 294 A6 | 11/1973 |
| FR | 2 399 811 A1 | 3/1979 |
| JP | 3031760 U | 12/1996 |
| JP | 2004-016732 A | 1/2004 |
| JP | 2004-041666 A | 2/2004 |
| WO | 95/03720 A2 | 2/1995 |
| WO | 97/03581 A1 | 2/1997 |
| WO | 00/53045 A1 | 9/2000 |
| WO | 2004/110197 A2 | 12/2004 |
| WO | 2007/016983 A1 | 2/2007 |

OTHER PUBLICATIONS

"Rollerblade TFS Skate Laces Micro", http://www.inlinewarehouse.com/viewlarge.html?PCODE=MILC, retrieved on Jan. 7, 2010, 1 page.

* cited by examiner

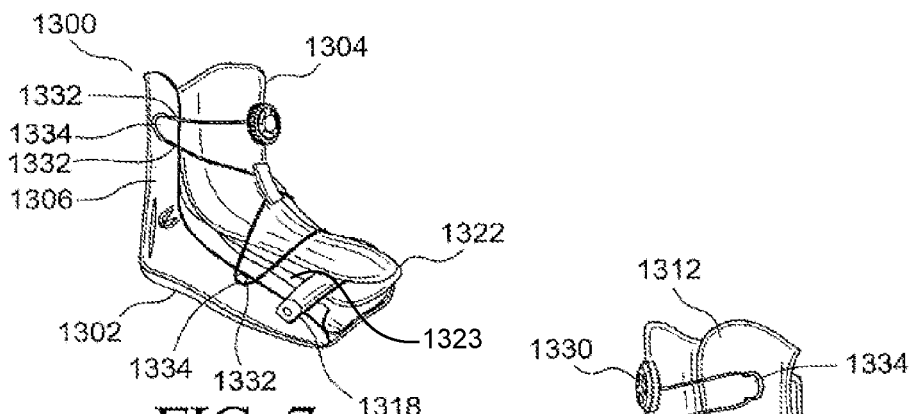
FIG. 7
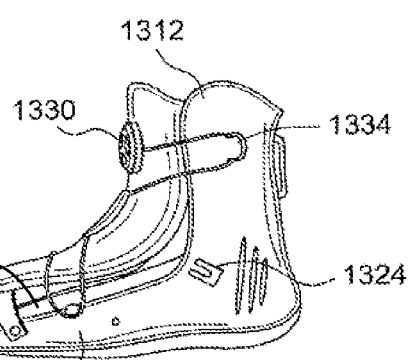
FIG. 10
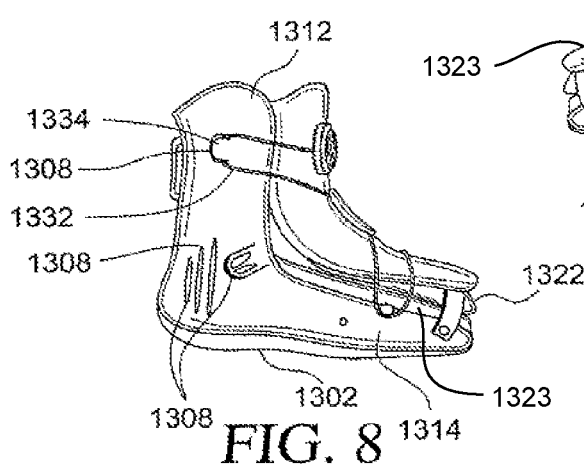
FIG. 8
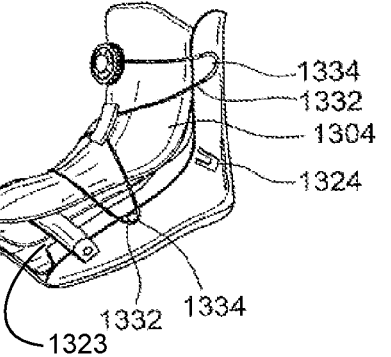
FIG. 11
FIG. 9

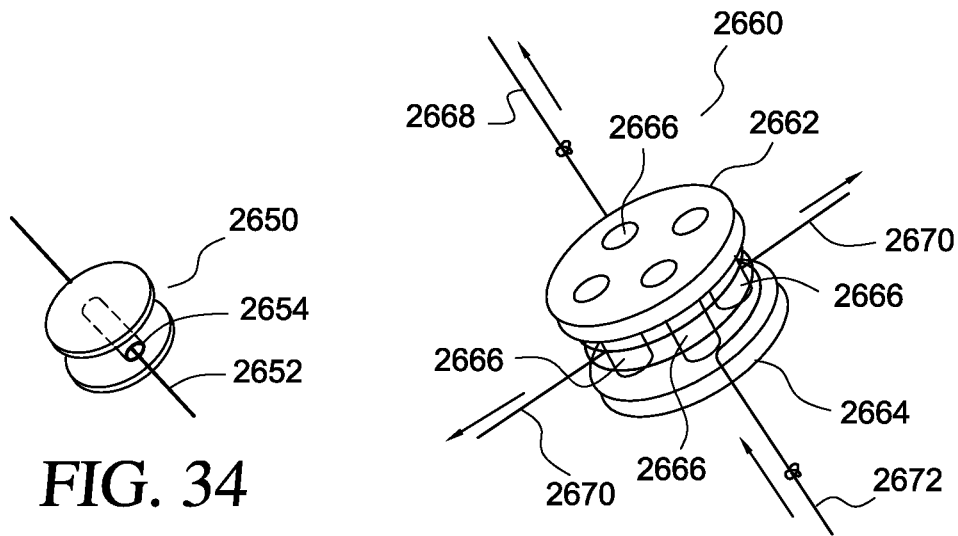
FIG. 34
FIG. 33
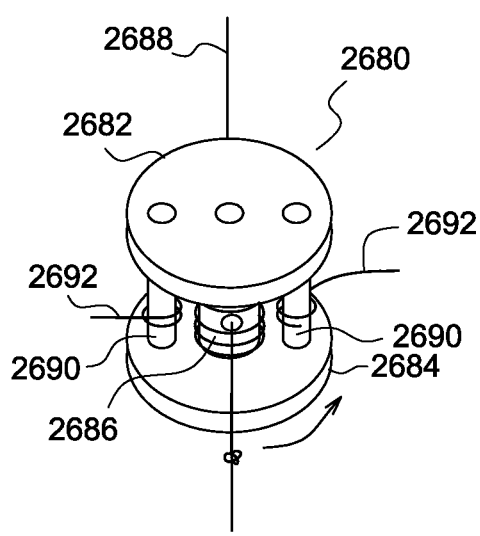
FIG. 35
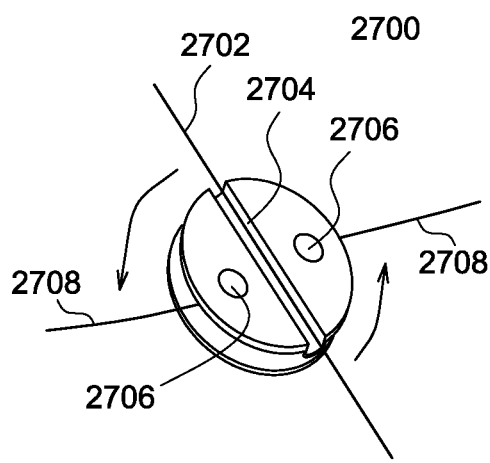
FIG. 36
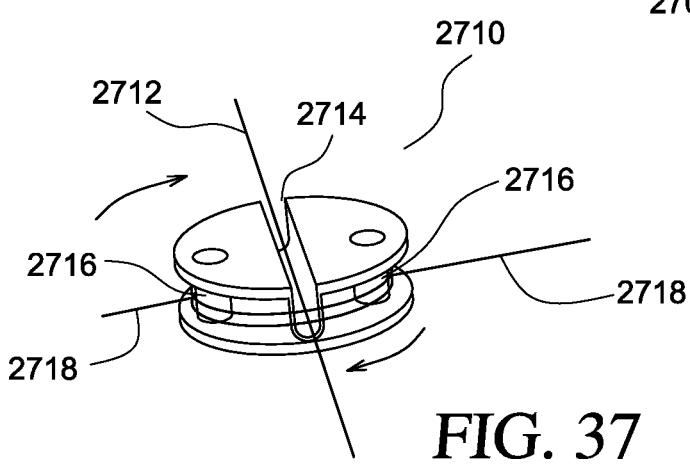
FIG. 37

ORTHOPEDIC DEVICES UTILIZING ROTARY TENSIONING

This application claims the benefit of U.S. application Ser. No. 12/466,597, filed May 15, 2009, which claims the benefit of U.S. Provisional Application No. 61/054,764, filed May 20, 2008, U.S. Provisional Application No. 61/054,766, filed May 20, 2008, U.S. Provisional Application No. 61/071,747, filed, May 15, 2008, and U.S. Provisional Application No. 61/092,297, filed Aug. 27, 2008.

FIELD OF THE INVENTION

The present invention relates generally to the field of orthopedic or prosthetic devices and more specifically to orthopedic devices utilizing rotary tensioning that provides ease of donning, doffing, and adjusting with the benefits of circumferential or wrap-around support and stabilization of the supported limb.

BACKGROUND

It is common that people, especially physically active and frail elderly people, experience a variety of limb injuries.

With regard to the foot and ankle, sprains to the calcaneofibular and anterior tabofibular ligaments often afflict a number of professional and amateur athletes. To aid in the proper healing and treatment of these and other lower leg and foot injuries it is necessary that the affected areas, as well as the surrounding tissue, be stabilized and immobilized.

Physicians traditionally have treated, and still currently treat, injuries affecting lower leg extremities and the foot by fitting the injured patient with the well-known, molded plaster or resin cast, which is set around inner cotton or gauze lining. The placement of this type of cast around the lower leg is time consuming, heavy, and costly. Further, this type of cast must not come into contact with water, which makes patient bathing difficult and time consuming. Additionally, if the cast needs to be removed for any reason, for example inspection or physical therapy, a whole new cast must be prepared and applied.

Alternatively, lower leg walkers provide stabilization and support of the lower leg, including the ankle and foot, such that at least partial mobility may be maintained while an injury to the lower leg, ankle, and/or foot is in the process of healing. Further, in contrast to the molded plaster or resin cast, a lower leg walker can be removed by the patient in order to bathe or for inspection of the injured limb by a physician or practitioner.

Existing wrap-around or circumferential walkers can be bulky and difficult and time consuming to don and doff. In particular, numerous straps must be properly threaded through retaining rings and each strap individually tightened in order to properly support and immobilize the limb.

With respect to the knee, knee braces are widely used to treat a variety of knee infirmities. Such braces may be configured to impart forces or leverage on the limbs surrounding the knee joint in order to relieve compressive forces within a portion of the knee joint, or to reduce the load on that portion of the knee. Moreover, in the event that knee ligaments are weak and infirm, a knee brace may stabilize, protect, support, unload, and/or rehabilitate the knee.

The knee is acknowledged as one of the weakest joints in the body, and serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any kind of physical activity requiring the use of the legs.

A healthy knee has an even distribution of pressure in both the medial and lateral compartments of the knee. It is normal for a person with a healthy knee to place a varus moment on the knee when standing so that the pressure between the medial and lateral compartments is uneven but still natural.

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or simply due to aging of the knee.

A major problem resulting from osteoarthritis of the knee is that the smooth cartilage lining the inside of the knee wears away. This leads to a narrowing of the joint space with the development of cysts and erosions in the bone ends. Because of the narrowing of the joint, bone comes directly in contact with bone, and an uneven distribution of pressure develops across the knee which may result in the formation of bone spurs around the joint. All of these changes ultimately lead to increasing pain and stiffness of the joint.

While there are no cures to osteoarthritis, there are many treatments. Individuals who have a diagnosis of isolated medial compartmental osteoarthritis of the knee are confronted with a variety of treatment options such as medications, surgery, and nonsurgical interventions. Nonsurgical interventions include the use of canes, lateral shoe wedges, and knee bracing.

Knee bracing is useful to provide compartment pain relief by reducing the load on the compartment through the application of an opposing external valgus or varus moment about the knee joint. Unloading knee braces have been shown to significantly reduce osteoarthritis knee pain while improving knee function.

While known knee braces are successful at reducing pain or at stabilizing a knee joint, many users find these braces to be bulky, difficult to don and properly tighten, complicated to configure, and uncomfortable to wear. For these reasons, an embodiment described herein has streamlined features capable of providing relief for medial or lateral compartmental osteoarthritis, or functional stability of the knee that is easy to don and properly tighten, without the attendant drawbacks of known unloading knee braces.

Accordingly, exemplary embodiments of a circumferential lower leg walker, and other orthopedic devices that alleviate or eliminate the above mentioned drawbacks are described herein.

SUMMARY

The orthopedic devices described herein may be, in exemplary embodiments, an offloading, lower leg walker. It is also contemplated that other orthopedic devices may utilize similar configurations as described below. Such additional orthopedic devices include but are not limited to wrist braces, ankle braces, knee braces, cervical collars, elbow braces, and any other orthopedic devices having strapping configurations.

The embodiments of a lower leg walker described herein typically take the form of a circumferential type walker, which provides support and stabilization to the lower leg by surrounding the lower leg, ankle, and foot with an appropriate supporting superstructure. It will be recognized that the features described herein may have applicability to other lower leg walker configurations or other types of orthopedic devices.

A first exemplary embodiment of a circumferential lower leg walker is in the form of a clam-shell like walker that has a dorsal shell hinged to an anterior portion of the walker. The dorsal shell is thus pivotably moveable away from and towards the posterior and side shells of the walker in order to open and close the walker in a clam-shell like manner. This configuration provides easy insertion and removal of the lower leg from the walker. Further, a tightening mechanism is provided that utilizes a lace or cable to simultaneously and incrementally tighten the components of the shell structure around the lower leg. Clearance holes can be provided in the shells to provide ventilation and weight savings.

In variations of the clam shell configuration walker, spacer fabrics or liners can be provided in some or all of the clearance openings in order to provide a more comfortable or close fit between the walker and the lower leg.

In a further variation, connection or retaining points for the cable of the tightening mechanism can be covered by the shell portions when the walker is in the closed configuration, so as to protect the retaining points and cable from damage.

In a further variation, the walker can have an open toe structure with the hinge portion of the dorsal shell connecting to the opposed side shell portions to surround the dorsal surface of the foot. An integral pump or inflation port can be positioned in a clearance hole of the shell to provide inflation to an inflatable liner or bladder. A fluid may also be utilized to provide hot or cold therapy through the inflatable bladder. The bladder may be formed with multiple chambers defined by welds therebetween with split openings in the welds to provide ventilation. Soft coverings may be applied to the shells, or a separate sleep cover may be utilized.

In a split dorsal shell embodiment of a circumferential walker, the dorsal shell is split into two or more components which are attached to the walker shell via a cable, retainers, and the tightening mechanism. The split dorsal shells are selectively attached to each other via a connector such as a zipper. When the dorsal shells are detached from each other, they may be flipped away from the opening of the walker to allow easy insertion of the lower leg therein.

In a side flap configuration of a circumferential walker, the dorsal shell is attached along one side to the walker shell via a cable, retainers, and the tightening mechanism. The dorsal shell is selectively attached to the walker shell along the other side via quick connect mechanisms. The quick connect mechanisms can be undone to allow the dorsal shell to be flipped away from the opening of the walker to allow easy insertion of the lower leg therein.

In another embodiment, the dorsal shell is completely removable from the walker. The tightening mechanism, cable, and retainers are all carried by the dorsal shell. The retainers have a quick connect structure that allows them to be selectively connected to the walker shell. Thus, the dorsal shell can be completely removed from the opening of the walker to allow easy insertion of the lower leg therein.

In a split back embodiment of a circumferential walker, the posterior shell is formed in three pieces that are connected to each other via suitable mechanisms, such as a strip of flexible material. The tightening mechanism, cable, and retainers are all carried by portions of the posterior shell. The wing portions of the posterior shell are selectively connected to the walker shell via quick connect mechanisms. Thus, the posterior shell can be completely removed or flipped away from the opening of the walker to allow easy insertion of the lower leg therein.

Similarly, a split dorsal shell configuration operates as just described, with the functions of the dorsal and posterior shells switched so that the dorsal shell can be completely removed or flipped away from the opening of the walker to allow easy insertion of the lower leg therein.

An overlapping dorsal shell configuration of a circumferential walker provides overlapping dorsal shell portions that are selectively attached to the walker shell via quick connect mechanisms. The tightening mechanism, cable, and retainers are all carried by the overlapping dorsal shell portions. Thus, the dorsal shell can be completely removed or flipped away from the opening of the walker to allow easy insertion of the lower leg therein.

In each of the exemplary embodiments, the tightening mechanisms provide quick and easy adjustment of the walker in order to provide the desired amount of support and stabilization to the lower leg.

In other exemplary embodiments, various configurations of quick tightening mechanisms and arrangements are utilized to provide quick and easy adjustment of the orthopedic device in order to provide the desired amount of support and stabilization to the lower leg.

For example, an orthopedic device may include a first member (posterior shell) and a second member (dorsal shell) corresponding to the first member. A rotary tensioning mechanism can be positioned on the second member and connected to at least one tensioning pulley positioned on the second member via at least one drive cable. At least one medial-lateral tensioning cable can extend between the tensioning pulley and the first member, such that rotation of the rotary tensioning mechanism in a first direction causes rotation of the at least one tensioning pulley to cause the at least one medial-lateral tensioning cable to draw the first and second members together.

Another exemplary embodiment of an orthopedic device disclosed herein may be of an unloading type knee brace, in accordance with the principles described in U.S. Pat. No. 7,198,610, granted Apr. 3, 2007, and U.S. publication nos. 2007/0185425A1, published Aug. 9, 2007, 2006/0135904A1, published Jun. 22, 2006, 2006/0135903A1, published Jun. 22, 2006, 2006/0135902A1, published Jun. 22, 2006, 2006/0135901A1, published Jun. 22, 2006, 2006/0135900A1, published Jun. 22, 2006, all commonly assigned and all herein incorporated in the entirety by reference.

The underlying principals of the above referenced patent and patent application publications are discussed in detail within each publication. The present disclosure focuses on a variation of such orthopedic devices disclosed in the above referenced patent and patent application publications. In particular, an orthopedic device in the form of a knee brace for stabilizing, protecting, supporting, unloading, and/or rehabilitating the knee is provided that utilizes a dial tensioning device to aid with tightening the force strap, and that further utilizes pull tightening mechanisms to aid with tightening each of the proximal and distal stability straps. The disclosed configuration provides an improved knee brace that is easy to properly tighten for all users via adjustment of the dial tensioning device and the pull tightening mechanisms.

Additional features of the knee brace may include padding or ventilated padding material provided as an interface between the proximal and distal shells and a user's body, or between the stability straps and the user's body. Further, openings, holes, or slots may be provided in any or all of the shells and straps to aid with ventilation, reduce weight, and/or provide flexibility.

The numerous other advantages, features and functions of embodiments of an orthopedic device having the features discussed herein will become readily apparent and better understood in view of the following description and accompanying drawings. The following description is not intended to limit the scope of the orthopedic device, but instead merely provides exemplary embodiments for ease of understanding.

BRIEF DESCRIPTION OF THE DRAWINGS

These and other features, aspects, and advantages of the present invention will become better understood with regard to the following description, appended claims, and accompanying drawings where:

FIGS. 7-11 represent side, front, and side perspective views of a further variation of the embodiments of a circumferential walker according to FIGS. 1-4;

FIG. 33 is a perspective view of a tensioning pulley for use with the embodiments shown in FIGS. 29, 30, and 31;

FIG. 34 is a perspective view of a tensioning pulley for use with the embodiment shown in FIG. 32;

FIG. 35 is a perspective view of another tensioning pulley for use with the embodiment shown in FIG. 32;

FIG. 36 is a perspective view of another tensioning pulley for use with the embodiment shown in FIG. 32;

FIG. 37 is a perspective view of another tensioning pulley for use with the embodiment shown in FIG. 32;

Figure 1:
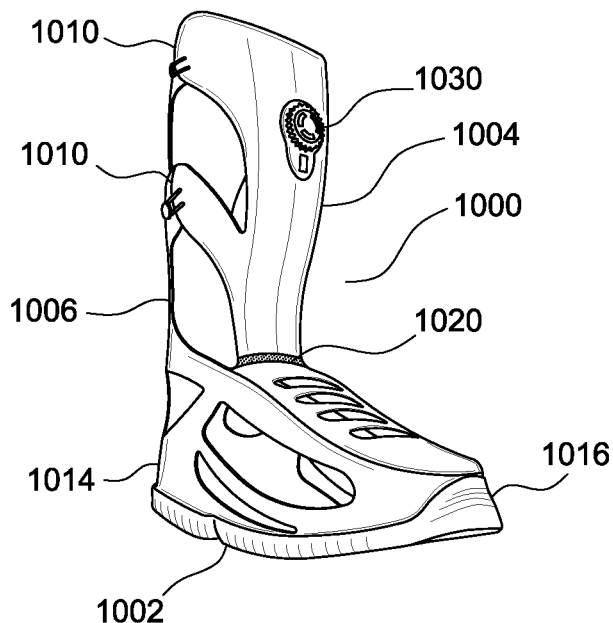
FIG. 1 is a front side, lower perspective view of an embodiment of a circumferential walker according to the present disclosure.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of orthopedic devices and the components thereof, and in no way limit the structures or configurations of the orthopedic devices and components thereof according to the present disclosure.

DETAILED DESCRIPTION

A. Environment and Context

Embodiments of an orthopedic device are provided for use in stabilizing and supporting the lower leg, foot, and ankle. In each of the embodiments, features that are provided one side of the device can easily be provided on the other side of the device. In this manner, it is intended that any of the embodiments of the orthopedic device described herein may be used on either right or left lower legs, with any appropriate reconfiguration of components that is deemed necessary for the proper fit and function of the device for the purpose of supporting and stabilizing either the left or right lower leg.

Another embodiment of an orthopedic device is provided to reduce the effect of osteoarthritis in a knee joint, or stabilize a knee joint that has been weakened by injury or other infirmities and that is convenient to don and properly tighten for all users, and in particular, users who are elderly or infirm. Although the illustrated embodiment shows the hinge positioned on the lateral side of the orthotic device and the stability straps positioned to extend around the medial side of the orthotic device, it will be understood that the orthotic device may be configured to reduce or cure both medial and lateral knee joint infirmities, and thus, the hinge may be positioned on the medial side of the orthotic device and the stability straps may be positioned on the lateral side of the orthotic device. It will also be recognized that the embodiments of a knee brace of the present disclosure may be used with either the right or left legs in order to provide relief for medial or lateral compartmental osteoarthritis, or functional stability for both right side and left side knee joints.

The embodiment of the disclosure is particularly adapted for a human knee joint, and may be dimensioned to accommodate different types, shapes and sizes of human joints and appendages. In addition, embodiments may be provided to orient principal forces exerted by strap systems of the embodiments at any desirable location to treat knee infirmities.

For explanatory purposes, the knee brace embodiment described herein is divided into sections which are denoted by general anatomical terms for the human body. Each of these terms is used in reference to a human leg which is divided in similar sections with a proximal-distal plane generally extending along the meniscus of the knee between the femur and tibia.

The embodiment of the knee brace is also divided into anterior and posterior sections by an anterior-posterior plane. The anterior-posterior plane generally corresponds to the coronal or frontal plane of a human leg. Each of the anterior and posterior sections is further divided about the center of the knee by a transverse or proximal-distal plane and median, sagittal or lateral-medial planes.

The anatomical terms described herein are not intended to detract from the normal understanding of such terms as readily understood by one of ordinary skill in the art of orthotics.

In each embodiment of the orthopedic devices described herein, a rotary type tensioning mechanism may be used to provide ease of tightening the device. Exemplary rotary type tensioning mechanisms are described in U.S. Pat. No. 5,934,599, granted August 1999, U.S. Pat. No. 6,202,953, granted March 2001, and U.S. Pat. No. 6,289,558, granted September 2001, and U.S. publication nos. 2003/0204938, published November 2003, 2006/0156517, published July 2006, 2007/0169378, published July 2007, 2008/0060167, published March 2008, 2008/0060168, published March 2008, 2008/0066272, published March 2008, 2008/0066345, published March 2008, 2008/0066346, published March 2008, and 2008/0083135, published April 2008, and all incorporated herein in the entirety by reference. Rotary tensioning devices as well as other suitable types of tensioning devices can also be used. Further exemplary tensioning devices are described in U.S. Pat. No. 7,198,610, granted April 2007, commonly owned, and herein incorporated in the entirety by reference.

The embodiments of the disclosure are adapted for supporting and stabilizing the lower leg or knee of human beings, and may be dimensioned to accommodate different types, shapes and sizes of human joints and appendages.

Exemplary materials and configurations for components of the orthopedic device, such as sole portions and shell portions, are described in detail in U.S. Pat. No. 5,078,128, granted January 1992, U.S. Pat. No. 5,329,705, granted July 1994, U.S. Pat. No. 5,378,223, granted Jan. 3, 1995, U.S. Pat. No. 5,464,385, granted November 1995, and U.S. Pat. No. 5,761,834, granted June 1998, all assigned to Royce Medical Co. and all incorporated herein in the entirety by reference. Additional exemplary configurations and materials are described in detail in U.S. Pat. No. 7,303,538, granted December 2007, assigned to Össur hf, and incorporated herein in the entirety by reference.

For further ease of understanding the embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing, however such support members or shells may have some degree of flexibility or resiliency.

Additionally, as used herein, the words "lace," "cable," and "wire" are used interchangeable and have their ordinary meanings and further describe an elongated member that is threaded through retention points and a tightening mechanism, and is used to provide tightening of the orthopedic device. Such "lace," "cable," and "wire" may refer to relatively long and relatively thin shaped metals or polymers, which may be single strand or multi-strand, and which may include friction reducing coatings thereon.

B. Detailed Description of a Clam-Shell Configuration Walker

A first embodiment of a circumferential lower leg walker having a clam-shell like configuration is shown in FIGS. 1-4. As can be seen from the figures, this embodiment opens and closes like a clam shell in order to provide easy access to the interior of the device for ease of donning and doffing the device, in particular for donning and doffing the device onto an injured limb.

The clam-shell like walker 1000 is configured in an essentially one-piece construction to provide a sleek and low profile device for use in stabilizing and supporting the lower leg and includes a tightening mechanism that provides incremental and simultaneous tightening of the walker about the lower leg. Numerous advantages are obtained from such a configuration, such as lower weight, and less opportunity for the device to catch on external objects or clothing. Any weight savings will be a substantial benefit, as a user must swing the mass of the walker, along with the leg, through the gait cycle. Additionally, the ease with which the tightening mechanism tightens the walker will aid users who may have trouble manipulating numerous and more complicated strap arrangements. In particular, elderly or infirm persons will be able to properly tighten the walker with ease.

The walker 1000 includes a semi-rigid, or substantially rigid shell configuration that is formed to support and surround the lower leg, foot, and ankle of a user. The shell configuration can extend from the foot and ankle up along the shin and tibia of the lower leg to a desired point below the knee joint. Exemplary suitable materials for forming the shells can include metals, such as aluminum, carbon, composite materials, such as carbon fiber/epoxy composites, glass fiber/epoxy composites, or suitable plastic materials, such as thermoplastic or thermosetting polymers, fiber reinforced plastic, molded chopped fibers, or any other suitable material. Other exemplary materials include, but are not limited to, nylons, glass filled nylon, polypropylenes, vinyls, polyvinyl chlorides, high density polyethylene, epoxies, urethanes, and polyesters.

The shell configuration includes a unitary dorsal shell 1004, a posterior shell 1006, and side shell portions 1014 extending along the lateral and medial sides of an outsole 1002. The side shell portions 1014 extend around the anterior of the walker 1000 to define a toe protector portion 1016. The outsole 1002 can be formed with suitable tread or other friction enhancing characteristics, and to provide the appropriate rocker sole type response associated with lower leg walkers. Any suitable material may be utilized to form the outsole 1002.

The dorsal shell 1004 is hinged to the toe protector portion 1016 via suitable mechanisms. As shown, the hinge 1018 is formed via a flexible plastic or elastomer, such as, for example, ethylene vinyl acetate (EVA). Of course, any suitable flexible material may be utilized, including silicone or natural or synthetic rubbers. Alternative hinge mechanisms, such as pivot pins and sleeves, or piano or butterfly hinges, can also be used.

The hinge 1016 allows the dorsal shell 1004 to flip open away from the posterior and side shell portions 1006, 1014. In this manner, a clam-shell like configuration is obtained to provide easier insertion or removal of an injured limb into or from the walker 1000.

Additionally, the dorsal shell 1004 can be formed with a further hinged portion 1020 between the shin/tibia portion and the foot portion in order to provide a comfort fit between the walker 1000 and the ridge of the foot and ankle. The hinge portion 1020 can be constructed in the same manner as the hinge 1018.

In order to further lighten the weight of the walker 1000, and/or to provide ventilation, material can be removed from areas of the shell portions to provide clearance holes 1008. The clearance holes 1008 can be formed in any of the shell portions and have any suitable size and/or shape.

In the exemplary configuration of the walker 1000 shown in FIGS. 1-4, each of the dorsal and posterior shells 1004, 1006 include wing portions 1010, 1012 that extend from the respective shell portions towards the opposed shell portion. The wing portions 1010, 1012 wrap around the leg in order to enclose and support the leg. The dorsal shell wing portions 1010 extend generally towards the posterior of the walker 1000 and the posterior shell wing portions 1012 generally extend towards the anterior of the walker 1000, such that corresponding dorsal and posterior wing portions generally overlap each other when the shells are brought together in a closed configuration and further define additional clearance holes 1108 between them in the closed configuration. The wing portions 1010, 1012 also serve as anchor points for a lace or cable 1032, and retainers 1034, as will be discussed in detail below.

The ease of donning and doffing the clam-shell like walker 1000 is further enhanced by the use of a tightening mechanism 1030 that allows each portion of the brace to be simultaneously incrementally tightened, without the need for numerous cumbersome straps. The tightening mechanism 1030 is positioned in a proximal area of the dorsal shell 1004, but can be positioned in any suitable location on the walker 1000.

As illustrated in FIGS. 1-4, the tightening mechanism 1030 can be a rotary type dial tensioner that, when rotated, either takes up or lets loose the cable 1032. The cable 1032 can be laced along the posterior surface of the dorsal shell 1004, or sandwiched within the dorsal shell 1004 between two suitable materials, such that the cable 1032 remains unobtrusive.

Figure 4:
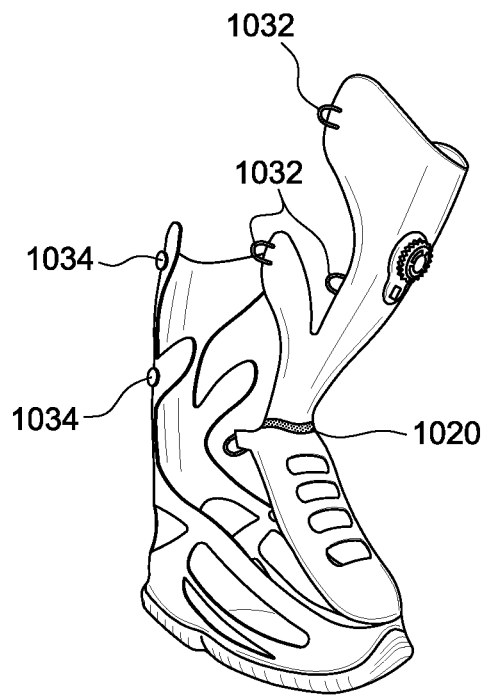
FIG. 4 is a front side, lower perspective view of the embodiment of FIGS. 1 and 4 with the laces or cables retracted.

As shown in FIG. 4, the cable 1032 can extend from the dorsal shell 1004 in the form of looped portions at different points along the shell. As previously mentioned, the wing portions 1010 of the dorsal shell 1004 can provide suitable areas from which the cable 1032 can extend. While three such looped portions are shown along each side of the walker 1000, it will be recognized that fewer or more looped portions may be utilized as needed.

In the open configuration, the looped portions of the cable 1032 can be minimized in size, by tightening or rotating the tightening mechanism 1030, in order to prevent interference of the cable 1032 with insertion of the lower leg into the walker 1000.

Figure 3:
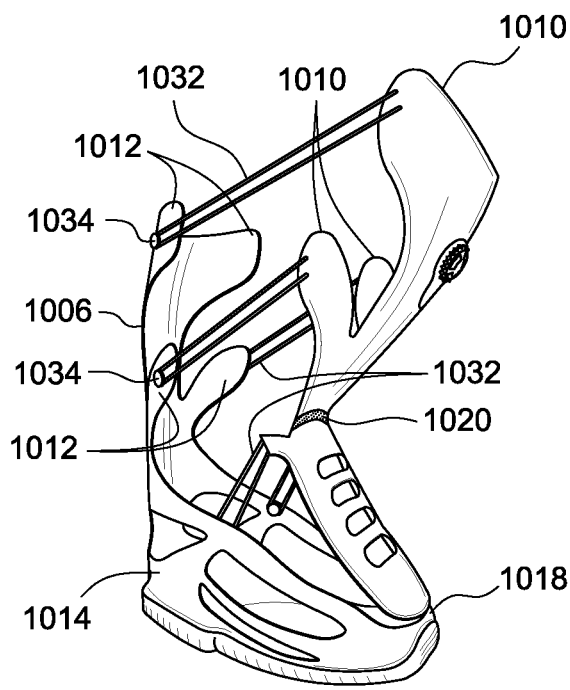
FIG. 3 is a front side, lower perspective view of the embodiment of FIG. 1 in an opened configuration.

As shown in FIG. 3, once the lower leg (not shown for ease of illustration) is inserted into the walker 1000, the looped portions of the cable 1032 can be extended, by releasing, loosening, or rotating the tightening mechanism 1030. The looped portions of the cable 1032 can be engaged with the retainers 1034 positioned on the posterior wing portions 1012 in order to provide a "quick connect" type configuration.

To effectuate such a quick connect configuration, the retainers 1034 may be provided in the form of hook type retainers with the protruding portion of the hook extending from the retainer towards the posterior of the walker 1000. Thus, the looped portions of the cable 1032 can be wrapped or looped over the protruding portion of the hooks. Alternative configurations may include any of the quick connect retainer configurations described herein below.

Figure 2:
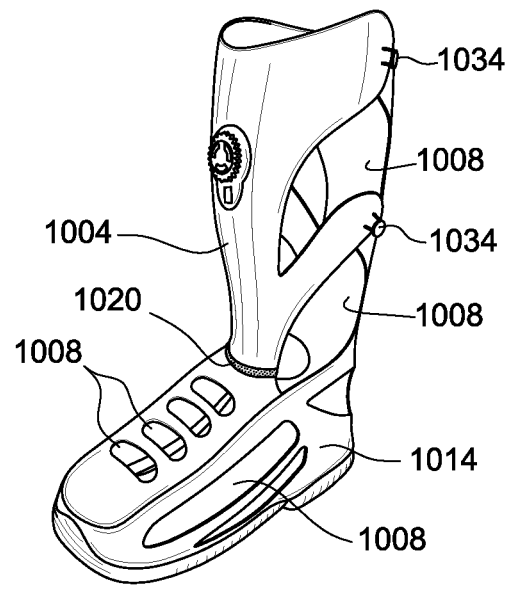
FIG. 2 is a front side, upper perspective view of the embodiment of FIG. 1.

As shown in FIGS. 1 and 2, once the looped portions of the cable 1032 have been appropriately engaged with the associated retainers 1034, the cable 1032 may be taken up to draw the dorsal shell 1004 into the closed configuration with the posterior shell 1006, such that the wing portions 1010, 1012 overlap to encircle the lower leg. The tightening mechanism 1030 is used to simultaneously tighten the cable 1032 throughout the walker 1000, so that the entire walker is easily tightened around the lower leg, without the need for manipulating and tightening numerous straps.

In order to remove the walker 1000 from the lower leg, the process is reversed, beginning with the release of the cable 1032 so that the dorsal shell 1004 can be flipped or pivoted away from the posterior shell 1006. Once the shells are in the open configuration and spaced from each other, the lower leg can be removed from the walker 1000.

As can be seen from the illustration and the above discussion, the clam shell like configuration with the cable tightening system provides a low profile walker with ease of donning, doffing, and tightening for adjustment.

Additional features, such as inflatable liners with integrally attached pumps, a foam midsole to control heel strike and roll over, and or a fabric exterior covering for the shell portions may also be provided.

Additionally, the shell portions may be formed from appropriately resilient materials or have particular resilient portions that allow the shell portions to better conform to the geometry of the user's lower leg. In such a case, the rigidity and stabilization for the support are provided via the tightening of the cable about the resilient portions.

Further variations and embodiments are described below.

C. Detailed Description of a Variation of a Clam-Shell Configuration Walker

Figure 5:
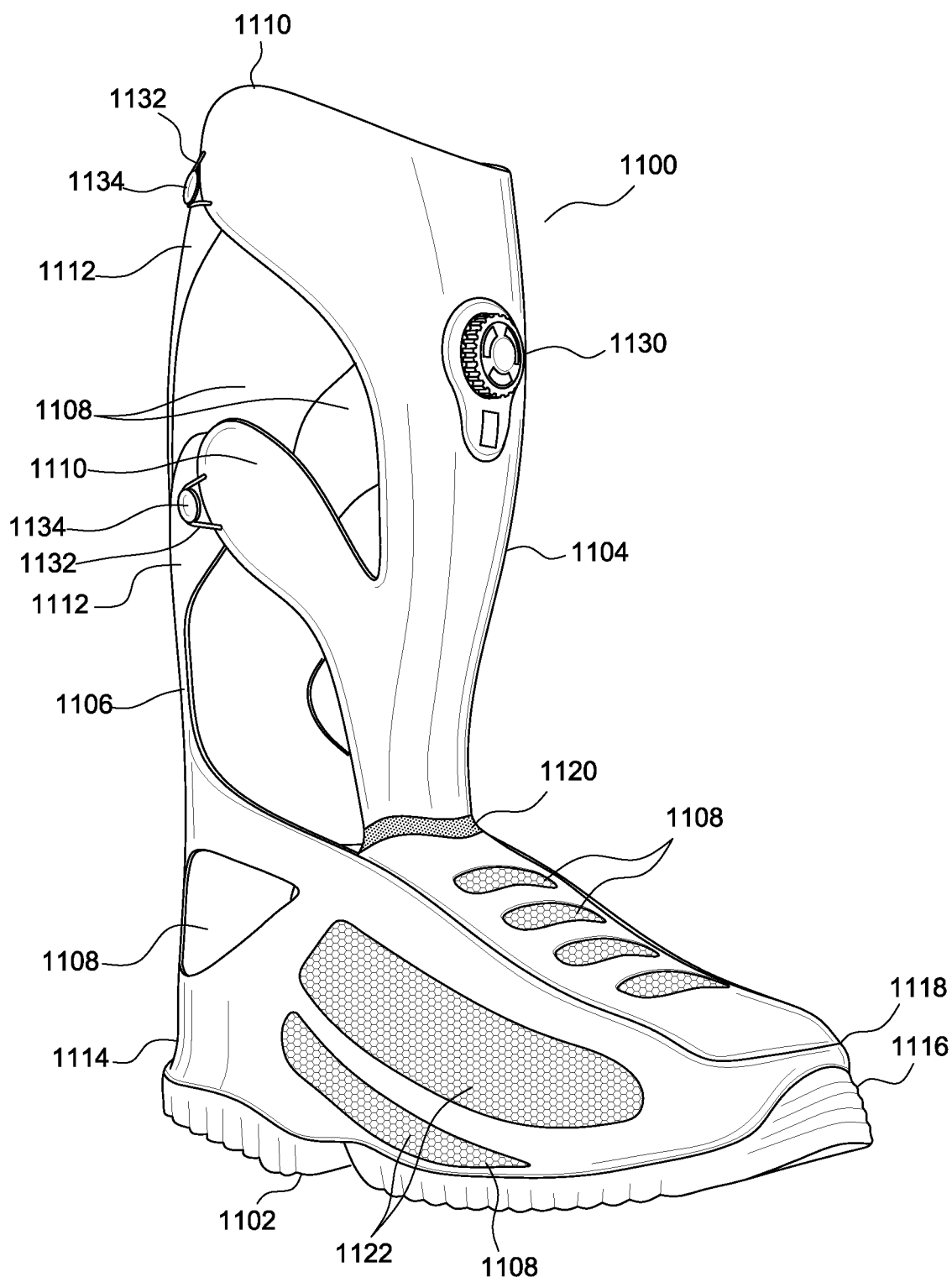
FIG. 5 is a front side, lower perspective view of a variation of the embodiment of FIGS. 1-4.

A variation of a clam-shell configuration lower leg walker is shown in FIG. 5. The walker 1100 can be made from the same materials as, is substantially the same as, and functions in substantially the same manner as the walker 1000 described above.

In particular, the walker 1100 includes an outsole 1102, a dorsal shell 1104, a posterior shell 1106, and side shell portions 1114. Again, dorsal and posterior shell wings 1110, 1112 extend from the dorsal and posterior shells 1104, 1106. As above, clearance holes 1108 are provided in the shell portions.

The side shell portions 1112, 1114 extend around the anterior of the walker 1100 to form a toe protector portion 1116. The outsole 1102 can extend over the side shell portions at the anterior of the walker 1100 in order to provide further toe protection.

The dorsal shell 1104 is hinged to the anterior portion of the walker 1100 at hinge portion 1118. A flexible hinge portion 1120 is also positioned along the midpoint of the dorsal shell 1120 in order to provide a more comfortable fit.

A tightening mechanism 1130 is positioned on the dorsal shell 1104 in order to tighten a cable 1132 that engages cable retainers 1134 as discussed in detail above.

In a variation from the embodiment of FIGS. 1-4, some of the clearance holes can be filled with a liner or spacer fabric 1122 to provide aerated cushioning for the foot within the walker 1100. Exemplary spacer materials are described in detail in U.S. publication nos. 2006/0135902, published June 2006, and 2007/0185425, published August 2007, both incorporated herein in the entirety by reference. Such a spacer fabric can provide additional comfort and a proper fit of the walker 1100.

A further variation of a clam-shell configuration walker is discussed next.

Figure 6:
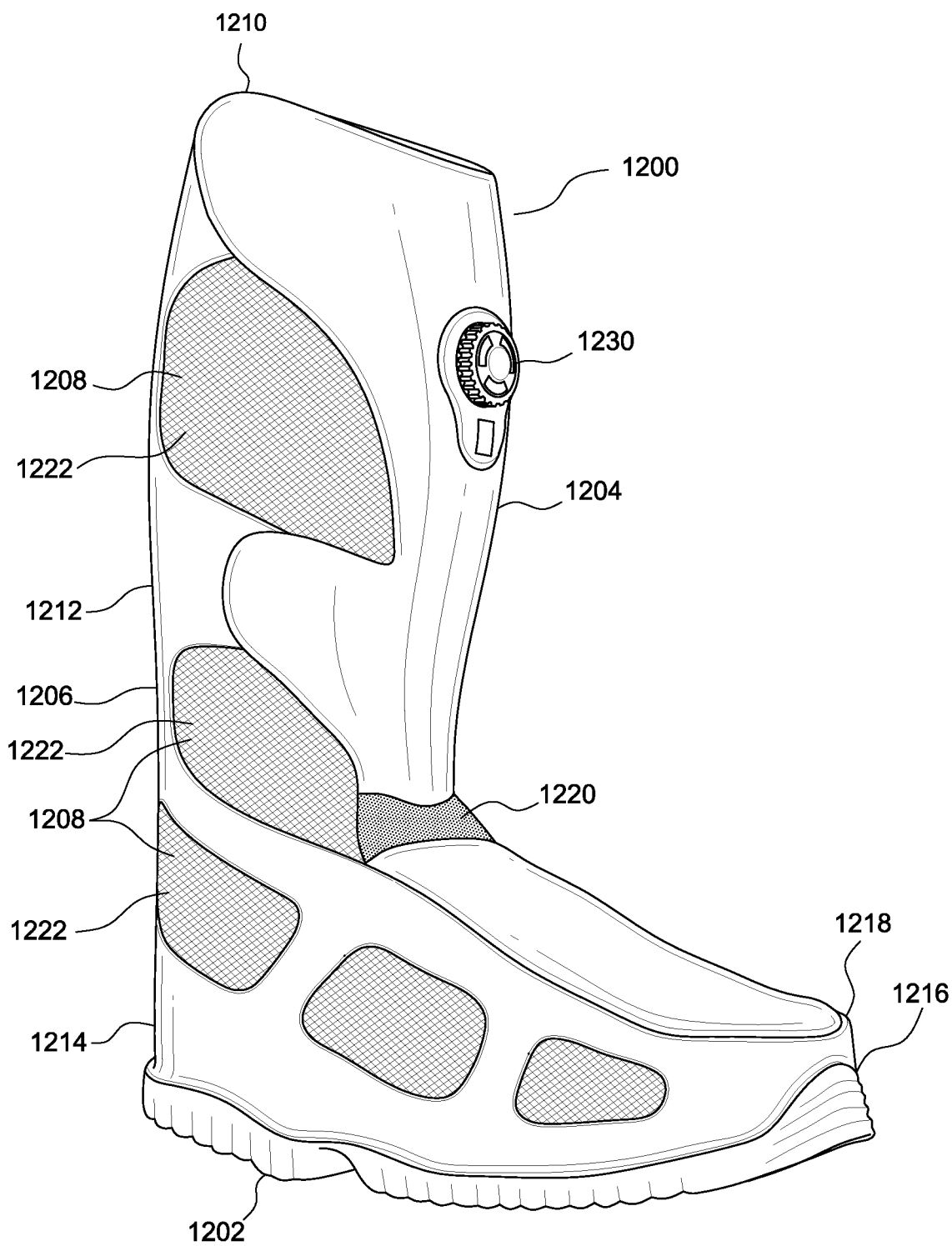
FIG. 6 is a front side, lower perspective view of a variation of the embodiment of FIGS. 1-4.

D. Detailed Description of a Further Variation of a Clam-Shell Configuration Walker Another variation of a clam-shell configuration lower leg walker is shown in FIG. 6. The walker 1200 can be constructed in substantially the same manner and to function in substantially the same way as the previously discussed walkers 1000, 1100.

Specifically, the walker 1200 includes an outsole 1202, a dorsal shell 1204, a posterior shell 1206, and side shell portions 1214, with clearance holes 1208 provided in the shell portions. Wing portions 1210, 1212 extend from the dorsal and posterior shells 1204, 1206.

A toe protector portion 1216 is formed by the side shell portions 1212, 1214 extending around the anterior of the walker 1200. The dorsal shell 1204 is hinged to the anterior portion of the walker 1200 at hinge portion 1218. A flexible hinge portion 1220 is also positioned along the midpoint of the dorsal shell 1220 in order to provide a more comfortable fit.

A tightening mechanism 1230 is positioned on the dorsal shell 1204 in order to tighten a cable that engages cable retainers as discussed in detail above. In a variation from the previous embodiments, the cable retainers of this embodiment can be positioned on the posterior wing portions 1212 such that they are covered or otherwise protected when the dorsal shell wing portions 1210 overlap the posterior wing portions 1212. In this manner, the cable and the cable retainers are hidden from view and protected when the shells are in the closed position. Accordingly, there is a reduced chance that the cable may accidentally come free from the cable retainers during use or that the cable or retaining members may be damaged.

In a further variation from the previous embodiments, all of the clearance holes can be filled with a liner or spacer fabric 1222 to provide aerated cushioning for the foot within the walker 1200. As discussed above, such a spacer fabric can provide additional comfort and a proper fit of the walker 1200.

Another variation of a clam-shell configuration walker is discussed next.

E. Detailed Description of a Further Variation of a Clam-Shell Configuration Walker Another variation of a clam-shell configuration lower leg walker is shown in FIGS. 7-11. The walker 1300 can be constructed from similar materials and function in substantially the same way as the previously discussed walkers 1000, 1100, 1200.

Walker 1300 includes a posterior shell 1306 that is formed as an open super structure support frame for surrounding the posterior portion of the lower leg and ankle, and the sides of the foot. The posterior shell 1306 has an outsole 1302 attached to or integrally formed along the plantar surface. Lateral and medial wing portions 1312 extend from the posterior shell 1306 towards the anterior of the walker 1300. Side shell portions 1314 extend from a distal portion of the posterior shell and wing portions 1306, 1312. Clearance holes 1308 are provided for ventilation, access, or to form cable retainers 1334, as will be discussed below.

A dorsal shell 1304 is formed to substantially conform to the dorsal aspects of the lower leg, ankle, and foot, and to close the walker 1300 in a clam-shell like manner, as previously discussed. In order to accomplish the clam shell closing, the dorsal shell 1304 is connected to the side shell portions 1314 in the anterior region of the side shells via hinges 1318. The hinges 1318 may be formed in any suitable manner, and as shown, are formed by pins rotating in the side shell portions 1314.

Similarly to walkers 1000, 1100, 1200, a tightening mechanism 1330 is positioned on the anterior surface of the dorsal shell 1304. A cable 1332 is routed across the anterior surface of the dorsal shell 1304 in connection with the tightening mechanism 1330 and retainers 1334.

As with the previous embodiments, the cable 1332 is looped through retainers 1334 in a quick connect manner. Specifically, at least some of the retainers can be integrated into the clearance holes 1308, by forming the clearance holes 1308 in a U-shape with the projection of the "U" extending towards the posterior of the walker 1300 so that the cable 1332 can be looped around the projection.

In this respect, the function and use of the walker 1300 is similar to those previously discussed. In an open configuration, the posterior shell 1306 and the dorsal shell 1304 define a clearance 1323 therebetween at least at a first end portion.

In addition to the features already described, the walker 1300 can have one or more inflatable liners 1322. The inflatable liners can be inflated or deflated via associated inflation ports or integrally carried pumps 1324. The inflation port or pump 1324 may be integrally carried in a clearance hole 1308 of the posterior shell 1306. A single pump can be provided to inflate all of the bladders simultaneously or individually to different pressures, or each bladder may be provided with an associated pump. The pumps are attached or carried by the walker 1300 so that they are not easily misplaced.

Further, the pumps or inflation ports can be configured to be usable with a fluid or liquid to provide hot and/or cold therapy.

The inflatable bladders can be configured to be ventilated by having slits passing through welded portions of the bladders. The welded portions can be used to create chambers within the bladders, and the use of more welded portions provides more chambers, as well as more slits to enable greater ventilation.

An additional feature is a midsole 1326 that can be formed with different materials or geometries to control heel strike, toe off, and energy return. An integrated adjustable heel platform or wedge can also be provided.

Further features may include providing a soft material covering over the shell portions or a sleep cover accessory to aid with preventing undesired contact with the hard surfaces of the walker 1300.

An embodiment of a split dorsal shell circumferential walker is described next.

F. Detailed Description of a Split Dorsal Shell Configuration Walker

Figure 12:
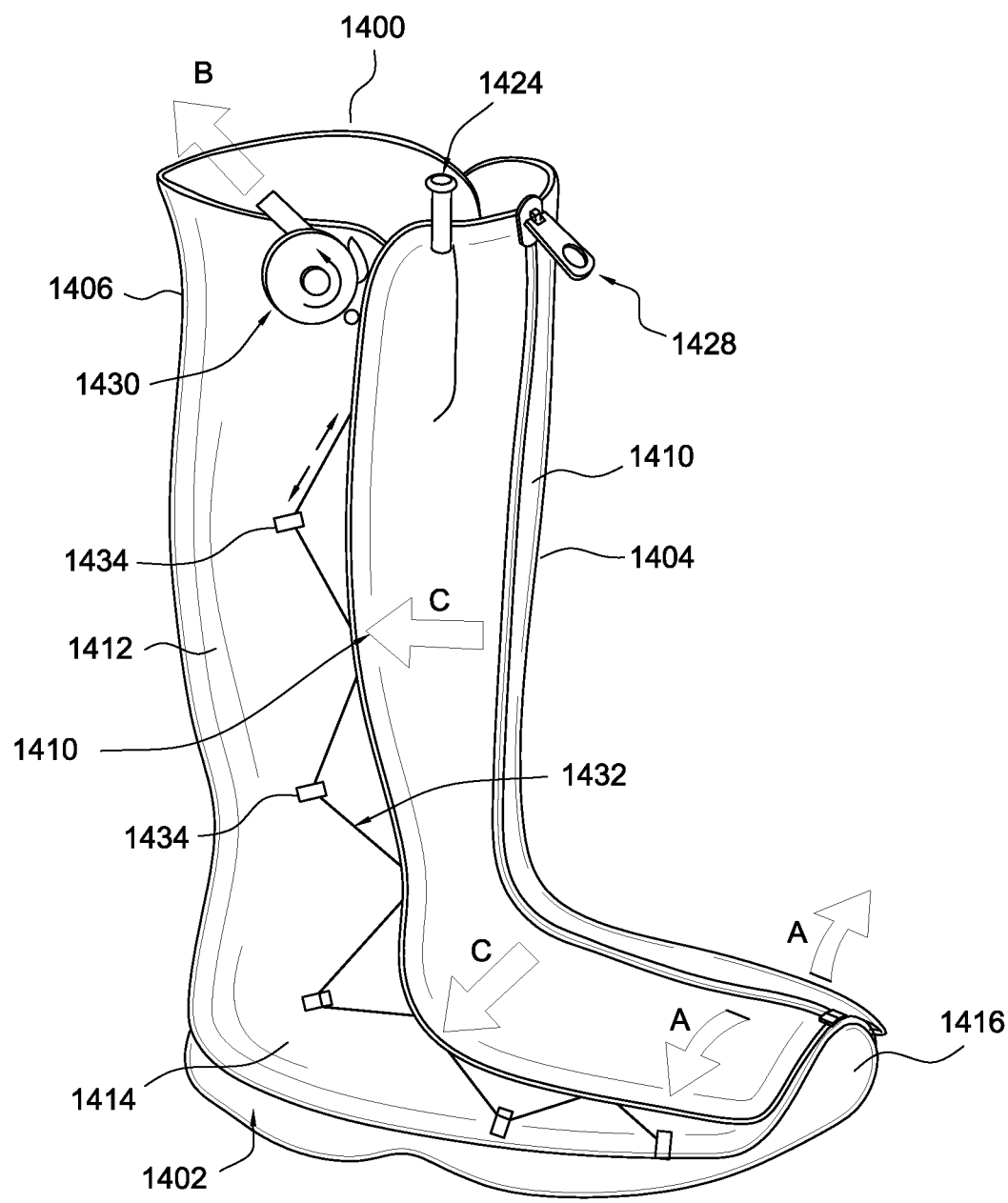
FIG. 12 represents a side perspective view of an alternate embodiment of a circumferential walker according to the present disclosure.

An embodiment of a split dorsal shell walker 1400 is shown in FIG. 12. The components of the walker 1400 can be formed from the same materials as the previously discussed walkers.

Additionally, the walker 1400 has generally the same configuration as the previously discussed walkers. In particular, a posterior shell 1406 is formed having wing portions 1412 and side shell portions 1414 that are integrated with or connected to an outsole 1402. The side shell portions 1414 and the outsole 1402 are configured to define a toe protector portion 1416 at the anterior portion of the walker 1400.

A dorsal shell 1404 is formed in two dorsal shell portions 1410 that are releasably connected to each other via connector 1428. As shown, the connector 1428 can be a zipper connection that may be zipped and unzipped in a recognized manner. When the zipper is zipped, the dorsal shell 1404 has a configuration that substantially corresponds to the dorsal aspects of the lower leg, ankle, and foot, and wraps around the anterior portions of the posterior side shell wings 1412 and the proximal portions of the side shells 1414.

Cable retainers 1434 are provided on the exterior surface of the wing portions and side portions 1412, 1414, and on the interior surfaces of the dorsal shell portions 1410. A cable 1432 is threaded through the retainers 1434 and connected to a tightening mechanism 1430. A single cable 1432 and tightening mechanism 1430 may be used, or one cable 1432 and tightening mechanism 1430 may be used along each of the lateral and medial sides of the walker 1400.

With the cable 1432 threaded through the retainers 1434, the dorsal shell portions 1410, are retained on the posterior shell wings and the side shells 1412, 1414. In order to place the user's lower leg within the walker 1400, the cable 1432 can be loosened by releasing the tightening mechanism 1430 and the zipper 1428 is unzipped so that the two dorsal shell portions 1410 can be detached from each other. Each of the dorsal shell portions 1410 can then be flipped open medially or laterally, respectively, as shown by arrows A. Thus, the dorsal aspect of the walker 1400 can be opened for placement of the lower leg, ankle, and foot therein.

Once the lower leg (not shown for ease of illustration) is positioned within the walker 1400, the dorsal shells 1410 can be flipped back to contact the dorsal aspects of the lower leg and reattached by zipping up the zipper 1428. The cable 1432 can next be tightened by manipulating or rotating the tightening mechanism 1430 to pull the cable 1432 in the direction indicated by arrow B. In this manner, when the cable 1432 is tightened, the dorsal shells 1428 are pulled away from the midline of the walker 1400, as shown by arrows C.

As with previous embodiments, to remove the lower leg from the walker 1400, the process is reversed.

Also like previous embodiments, an inflatable liner or bladder (not illustrated) can be placed within the walker 1400 to provide compression therapy and/or to aid with properly fitting the walker 1400 to the lower leg. The inflatable liner can be inflated via the use of the integrated dual action micro pump 1424.

It can be seen that the split dorsal shell configuration provides an alternate method of providing ease of donning, doffing, and tightening the walker, without the use of numerous and complicated strap configurations.

Variations of a side flap configuration for a circumferential lower leg walker are discussed next.

G. Detailed Description of a Side Flap Configuration Walker

Figure 13:
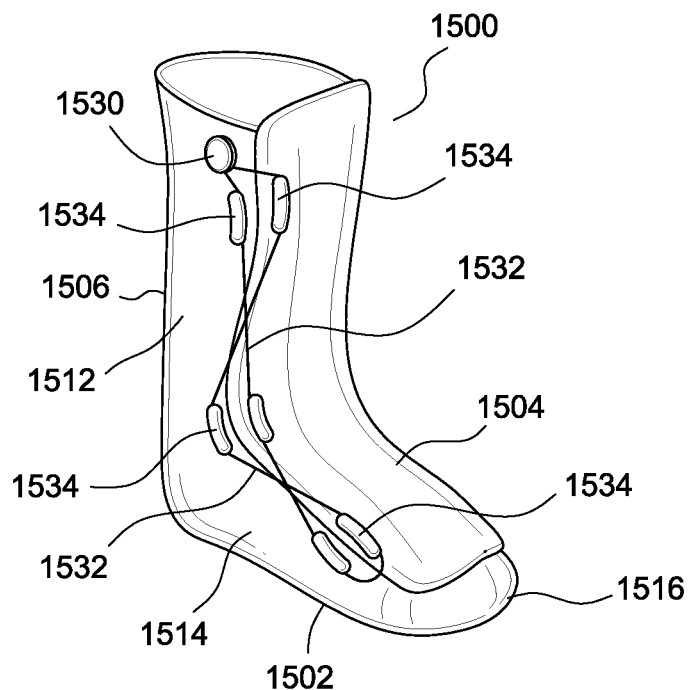
FIG. 13 represents a front side perspective view of an alternate embodiment of a circumferential walker according to the present disclosure.
Figure 14:
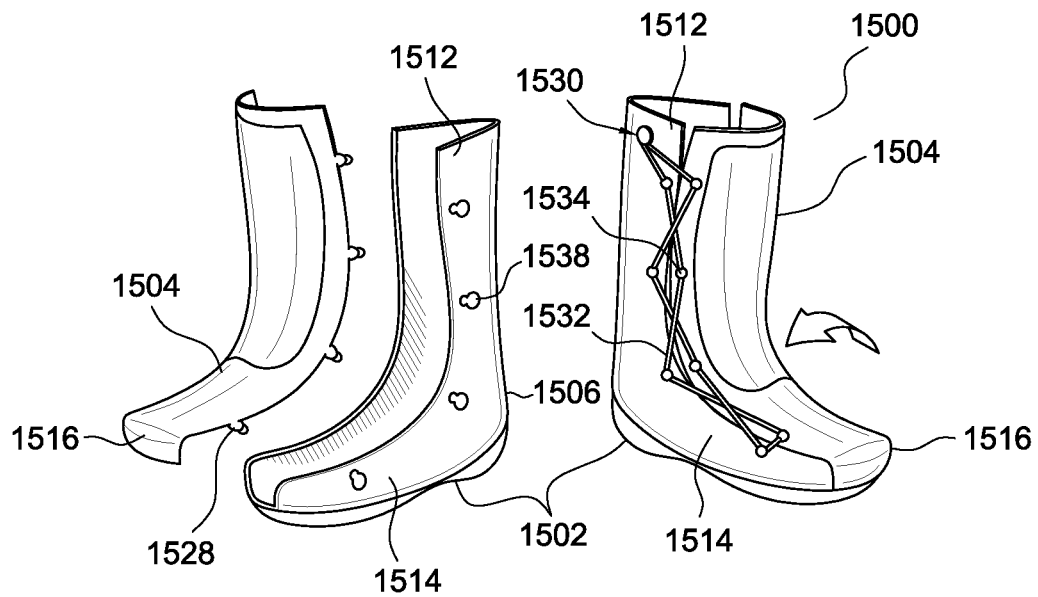
FIG. 14 represents left and right front side perspective views of a variation of the embodiment of FIG. 13.

Variations of a side flap configuration for a circumferential lower leg walker 1500 are shown in FIGS. 13 and 14. The walker 1500 can be formed from the same materials, in a similar configuration, and can function in a similar manner as previously discussed walkers.

Accordingly, the walker 1500 includes a posterior shell 1506 with wing portions 1512, and side shell portions 1514 attached to or integral with an outsole 1502, and extending around the anterior of the walker 1500 to define a toe protector portion 1516.

Alternatively, as shown in FIG. 14, the side shell portions 1514 can end prior to the anterior portion of the walker 1500 and the toe protector portion 1516 can be defined by a depending portion of the dorsal shell 1504.

The dorsal shell 1504 is shaped and configured to correspond to the dorsal aspects of the lower leg, ankle, and foot, and to overlap the wing and side shell portions 1512, 1514. Along one side of the walker 1500, the dorsal shell 1504 is connected to the walker 1500 via a cable 1532 that is threaded through retainers 1534 arranged on the exterior surfaces of the wing and side shell portions 1512, 1514 and the dorsal shell 1504. The retainers can be fixed to the shells or removably attached in any manner described herein. The cable is connected to a tightening mechanism 1530 attached to a side of the walker 1500 for tightening and loosening in a manner discussed above.

Along the opposed side of the dorsal shell 1504 from the cable 1532, the dorsal shell is removably attached to the wing and side shell portion 1512, 1514 along that side. The attachment may take the form of a zipper connection as discussed above with respect to the walker 1400.

Alternatively, as shown in FIG. 14, the attachment may take the form of quick connect connectors 1528 that are removably received in receiver portions 1538 in the wing and side shell portion 1512, 1514 along that side. The receiver portions 1538 can include an enlarged portion and a reduced portion such that the head of the connectors 1528 can be passed through the enlarged portion of the receiver portions 1538 and then engaged with the reduced portion of the receiver portions 1538. Exemplary connectors and receiver portions are described in detail in U.S. publication nos. 2006/0135902, published June 2006, and 2007/0185425, published August 2007, both previously incorporated herein by reference.

In use, the cable 1532 can be loosened and the connectors 1528 or zipper released or unzipped so that the dorsal shell 1504 can be flipped over to open the walker 1500. The lower leg can then be placed therein and the dorsal shell 1504 flipped back to cover the dorsal aspects of the lower leg and the connectors 1528 connected or the zipper zipped up to engage the dorsal shell 1504 to the wing and side shell portion 1512, 1514 along that side.

The cable 1532 can next be tightened in the manner previously discussed to provide proper fit, support and stabilization to the lower leg. Of course, the process can be reversed in order to remove the lower leg from the walker 1500.

The number of connectors 1528 and lace retainers 1534 can be varied as desired in order to provide the desired amount of strength and rigidity to the walker 1500.

A removable dorsal shell configuration walker is discussed next.

H. Detailed Description of a Removable Dorsal Shell Configuration Walker

Figure 15:
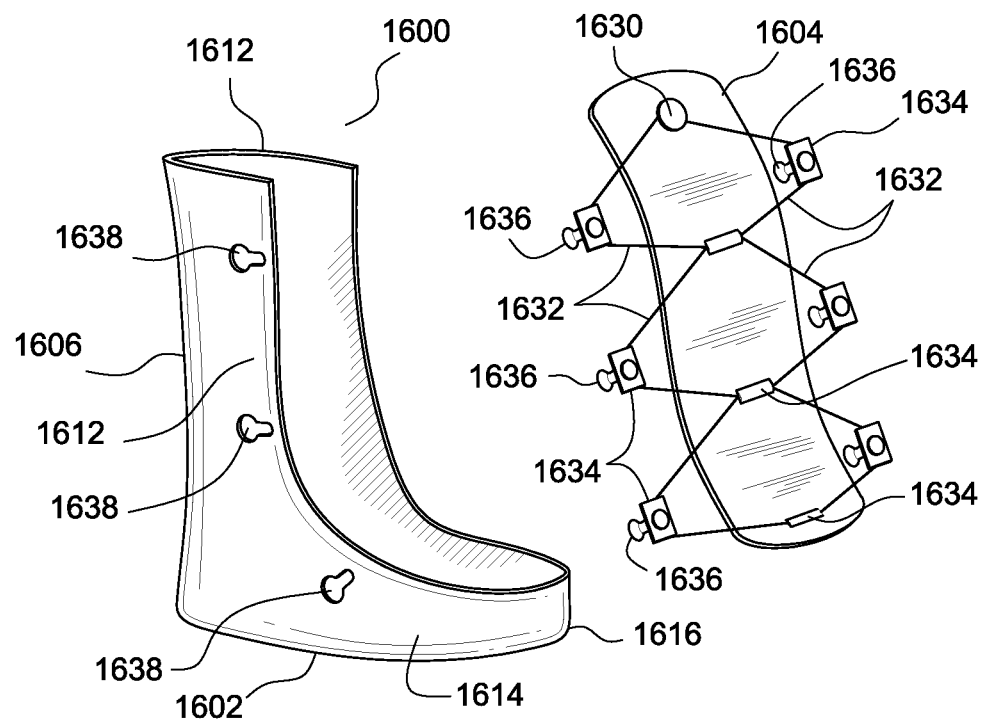
FIG. 15 represents a side perspective view of another embodiment of a circumferential walker according to the present disclosure.

The walker 1600 shown in FIG. 15 is a removable dorsal shell configuration that can be constructed from similar materials, in a similar configuration, and to function in a similar manner as previously discussed walkers.

Accordingly, an outsole 1602 is attached to or integrally formed with a posterior shell 1606 having wing and side shell portions 1612, 1614 extending towards and around the anterior of the walker 1600 to form a toe protector portion 1616.

A wholly detachable and reattachable dorsal shell 1604 is configured to correspond to the dorsal aspects of the lower leg, ankle, and foot, and to overlap the wing and side shell portions 1612, 1614.

A tightening mechanism 1630, cable 1632, and retainers 1634 are arranged along the anterior surface of the dorsal shell 1604. Additional retainers 1634 are positioned within loops formed by the cable 1632. The loops and retainers 1634 extend away from the dorsal shell 1604 and the retainers 1634 include connector portions 1636 that are configured to be connected to receiver portions 1638 positioned along the wing and side shell portions 1612, 1614.

The connector and receiver portions 1636, 1638 can be configured as discussed above. Alternatively, the connections can be achieved via other mechanisms, such as hook and loop connections or snap connectors.

The operation of the removable dorsal shell embodiment is as follows. The cable 1632 is loosened, and the retainers 1634 are disengaged from the walker 1600 so that the dorsal shell 1604 can be removed from the walker 1600. Thus, the walker is in an open configuration which allows the lower leg to be inserted therein.

Once the lower leg is positioned within the walker 1600, the dorsal shell 1604 can be reattached to the walker 1600 by connecting the retainers 1634 to the walker 1600. Once the retainers 1634 have been connected, the cable 1632 can be tightened in a manner discussed above.

To remove the lower leg from the walker 1600, the process is reversed.

As can be seen, the complete removal of the dorsal shell from the walker provides a completely free opening in which to insert the lower leg into the walker without causing pain to an injured limb. The tightening mechanism also provides a quick manner of tightening the walker around the lower leg in order to provide the necessary support and stabilization.

Next, a split back configuration lower leg walker is discussed.

I. Detailed Description of a Split Back Configuration Walker

Figure 16:
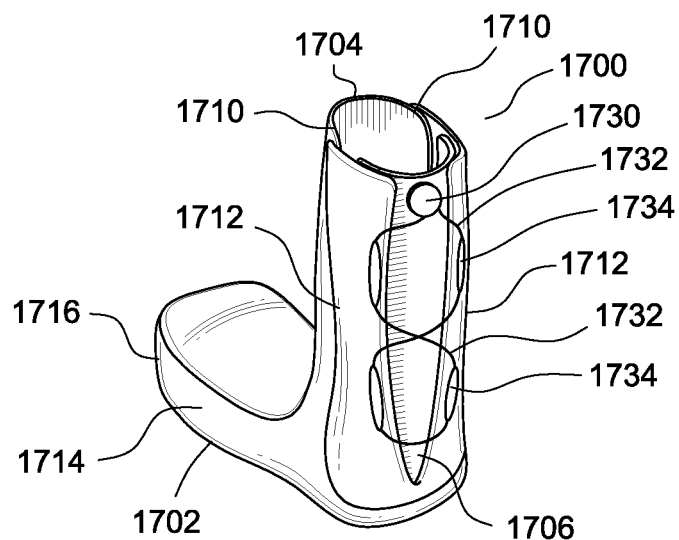
FIG. 16 represents a rear side perspective view of a further embodiment of a circumferential walker according to the present disclosure.
Figure 17:
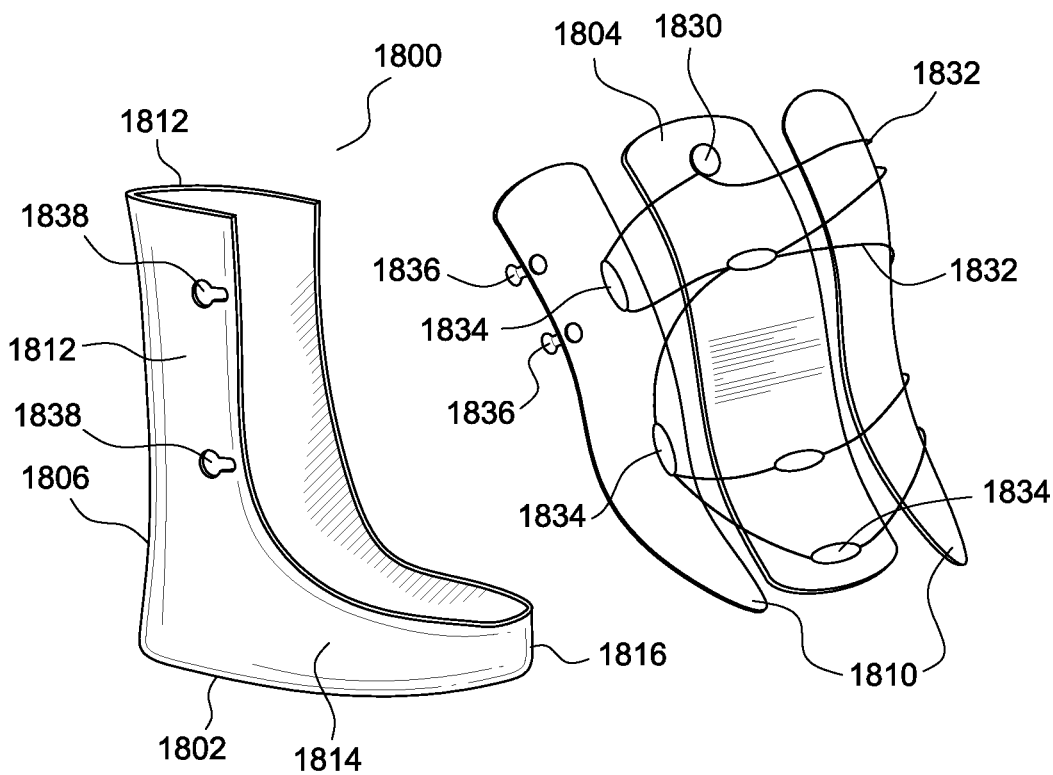
FIG. 17 represents a side perspective view of another embodiment of a circumferential walker according to the present disclosure.

A split back configuration walker 1700 is shown in FIG. 16 having a similar construction from similar materials as previously discussed with regard to other walker embodiments.

The walker 1700 is configured as a rear entry walker with an insertion recess defined between an outsole 1702 attached to or integrally formed with side shells 1714 and a dorsal shell 1704 having wing portions 1710 extending towards the posterior of the walker 1700. A toe protector portion 1716 is formed on the anterior of the walker 1700 via the side shells 1714 and the dorsal shell 1704.

Additionally, a completely removable, split posterior shell 1706 having wing portions 1712 is arranged to surround and support the anterior of the lower leg. The posterior wing portions 1712 are attached to the posterior shell 1706 via suitable connection mechanisms, such as a flexible fabric or material to form an integral, split, posterior shell portion. The posterior wing portions 1712 are removably attached to the wing portions 1710 of the dorsal shell 1704 in any suitable manner discussed herein above or below.

A tightening mechanism 1730 is carried on the proximal portion of the posterior shell 1706. Retainers 1734 are carried along the posterior surfaces of the posterior wing portions 1712. A cable 1732 is threaded through the retainers and connected to the tightening mechanism 1730.

In use, the cable 1732 is loosened and one or both of the posterior wing portions 1712 are detached from the wing portions 1710 of the dorsal shell 1704 in order to flip the posterior shell portion 1706 away from the opening or to completely remove the posterior shell portion 1706.

Once the opening is exposed, the lower leg is inserted therein, and the posterior wing portion or portions 1712 are reattached to the wing portions 1710 of the dorsal shell

1704. The cable 1732 can then be tightened in a manner as previously discussed to provide the appropriate support and stabilization to the lower leg.

In order to remove the lower leg from the walker 1700, the process is reversed.

In view of the above, the complete removal of the posterior shell from the walker provides a completely free opening in which to insert the lower leg into the walker without causing pain to an injured limb. The tightening mechanism also provides a quick manner of tightening the walker around the lower leg in order to provide the necessary support and stabilization.

In an alternate configuration, the posterior shell can be hinged to the walker in a manner similar to those discussed above so that the posterior shell provides a clam-shell like configuration with the dorsal shell.

Next, variations of a split dorsal shell configuration walker are discussed.

J. Detailed Description of a Split Dorsal Shell Configuration Walker

Variations of a split dorsal shell configuration walker 1800 are shown in FIGS. 17-20 having similar constructions from similar materials as previously discussed with regard to other walker embodiments.

Accordingly, an outsole 1802 is attached to or integrally formed with a posterior shell 1806 having wing portions 1812 and side shell portions 1814 that can extend to form a toe protector portion 1816 at the anterior of the walker 1800.

Figure 18:
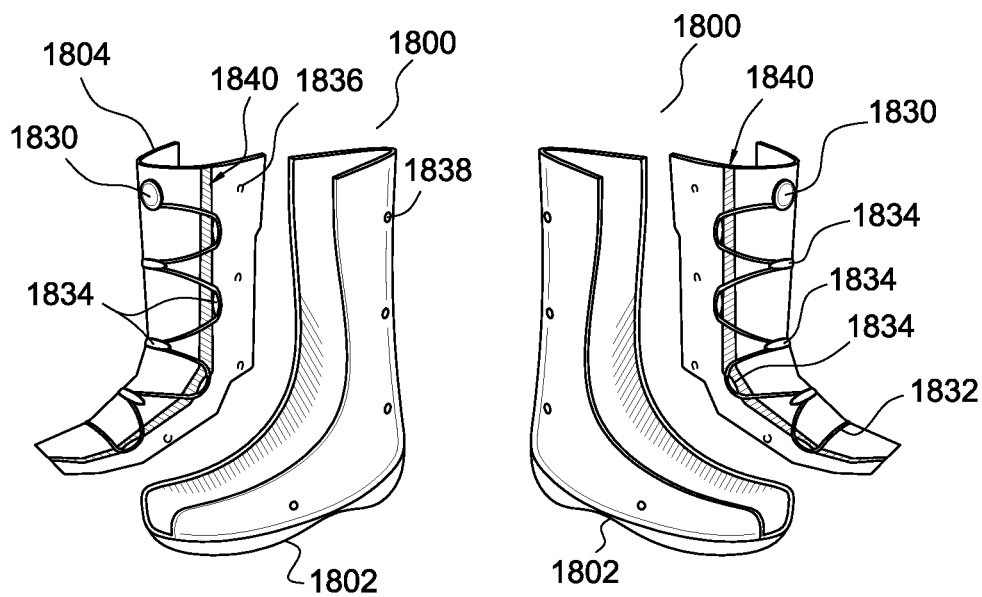
FIG. 18 represents left and right front side perspective views of a variation of the embodiment of FIG. 17.
Figure 19:
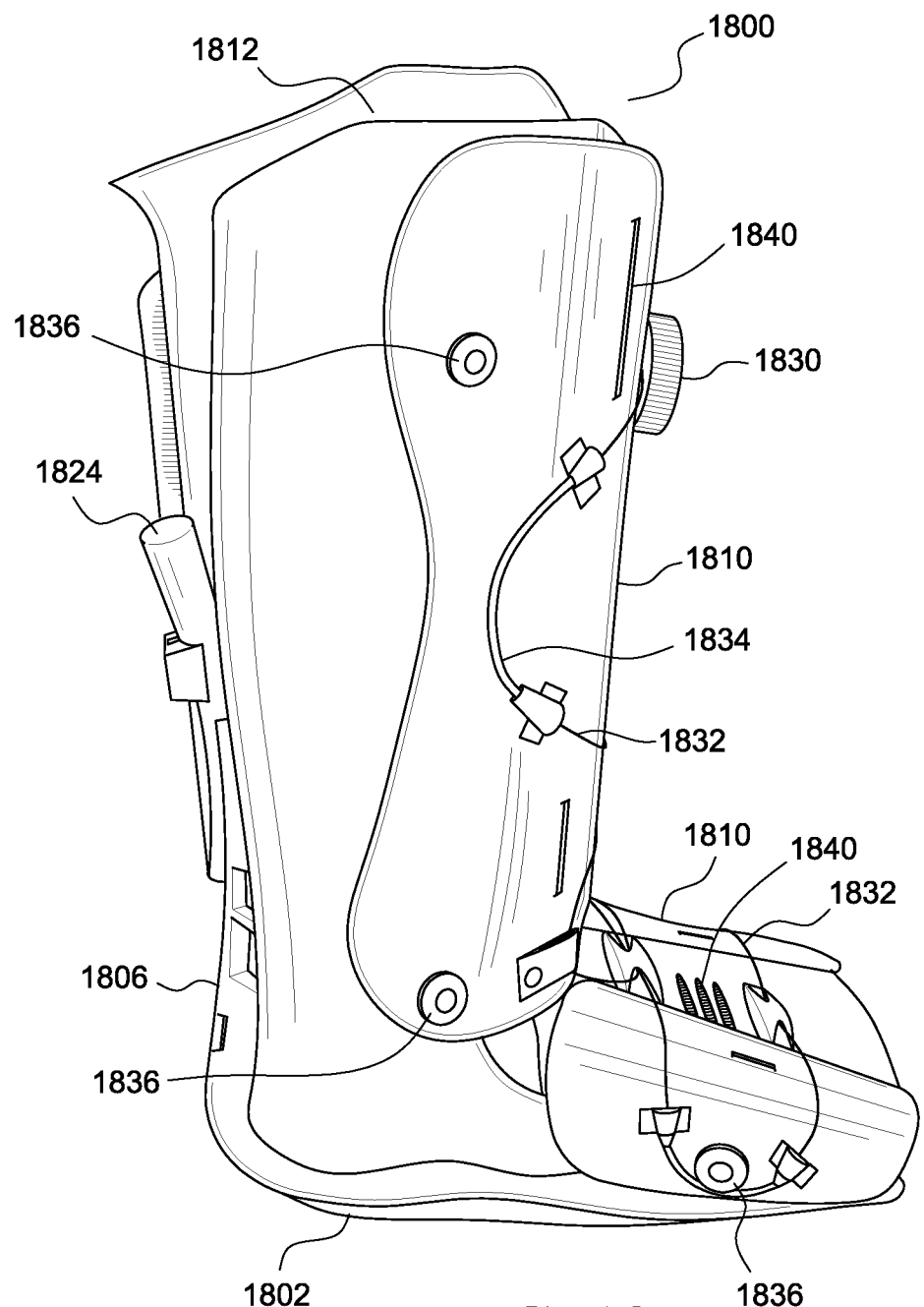
FIG. 19 represents a side view of yet another variation of the embodiment of FIG. 17.
Figure 20:
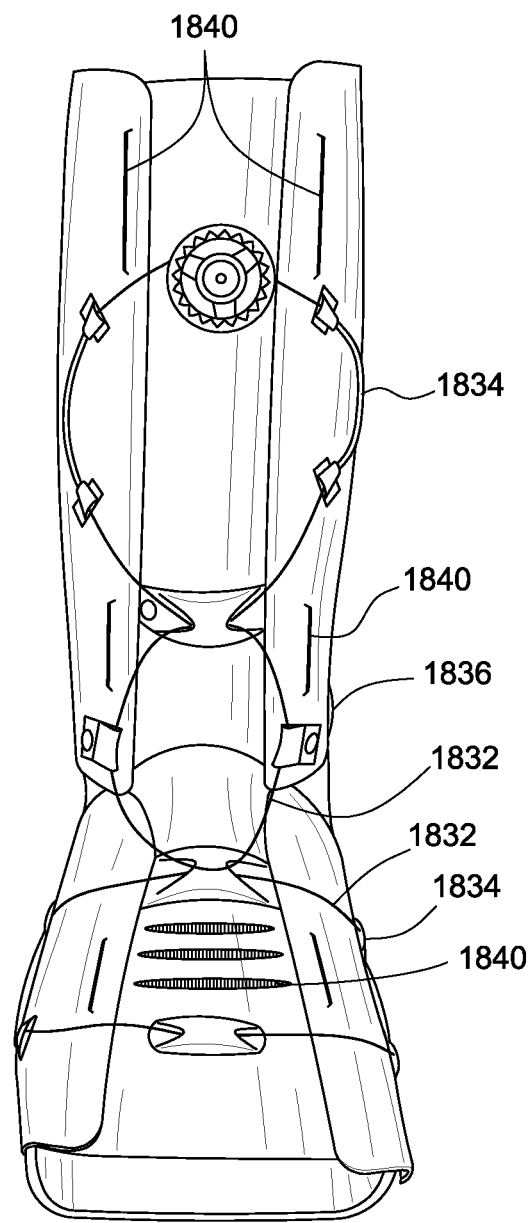
FIG. 20 represents a front view of the embodiment of FIG. 19.

It is noted that in alternate configurations shown in FIGS. 18-20 that the toe protector portion is not provided, or may be provided via a downward extending portion of the dorsal shell in a manner as discussed above.

A completely removable split dorsal shell 1804 having wing portions 1810 is configured to correspond to the dorsal aspects of the lower leg, ankle, and foot, and to overlap the wing and side shell portions 1812, 1814.

As shown in FIG. 18, the wing portions 1810 are connected to the dorsal shell 1804 via a flexible fabric or material 1840. Of course, alternate connection mechanisms, such as zippers or hook and loop fasteners may also be used.

For example, as shown in FIGS. 19-20, the connectors 1840 can be formed of respective sections of hook and loop material that are selectively engageable and disengageable from each other. Another variation in FIGS. 19-20 is that the wing portions 1810 of the dorsal shell 1804 are formed in distinct proximal and distal portions. Further, at least one integral pump and/or inflation port 1824 is carried by the posterior shell 1812 for inflating an inflatable bladder (not shown).

The dorsal shell of the embodiment of FIGS. 17-20 is similar in configuration to the split posterior shell of the embodiment of FIG. 16. Thus, the dorsal shell 1804 carries a tightening mechanism 1830 and the dorsal wing portions 1810 carry retainers 1834. A cable 1832 is threaded among and between the retainers 1834 and connected to the tightening mechanism 1830 for operation as previously discussed.

The dorsal wing portions 1810 are configured to be removably connected to the posterior wing portions 1812 and side shell portions 1814 in any suitable quick connect manner previously discussed. In particular, the dorsal wings 1810 can carry connectors 1836 that are received in slots 1838 in the posterior wing portions 1812 and side shell portions 1814.

The operation of the split dorsal shell configuration walker is substantially similar to the operation of the split back configuration walker. The cable 1832 is loosened and one or both of the dorsal wing portions 1810 are detached from the walker 1800 to either flip the dorsal shell 1804 away from the opening or to completely remove the dorsal shell 1804. Alternatively, the dorsal shell 1804 can be hinged to the walker 1800 in a manner discussed above.

Once the opening to the walker 1800 is exposed, the lower leg can be easily inserted into the walker 1800. Next, the dorsal wing portions 1810 are reattached to the walker 1800, and the cable 1832 is tightened as previously discussed to provide the desired amount of support and stability to the lower leg.

In view of the above, the complete removal of the dorsal shell from the walker provides a completely free opening in which to insert the lower leg into the walker without causing pain to an injured limb. The tightening mechanism also provides a quick manner of tightening the walker around the lower leg in order to provide the necessary support and stabilization.

Next, an overlapping dorsal shell configuration walker is described.

K. Detailed Description of an Overlapping Dorsal Shell Configuration Walker

Figure 21:
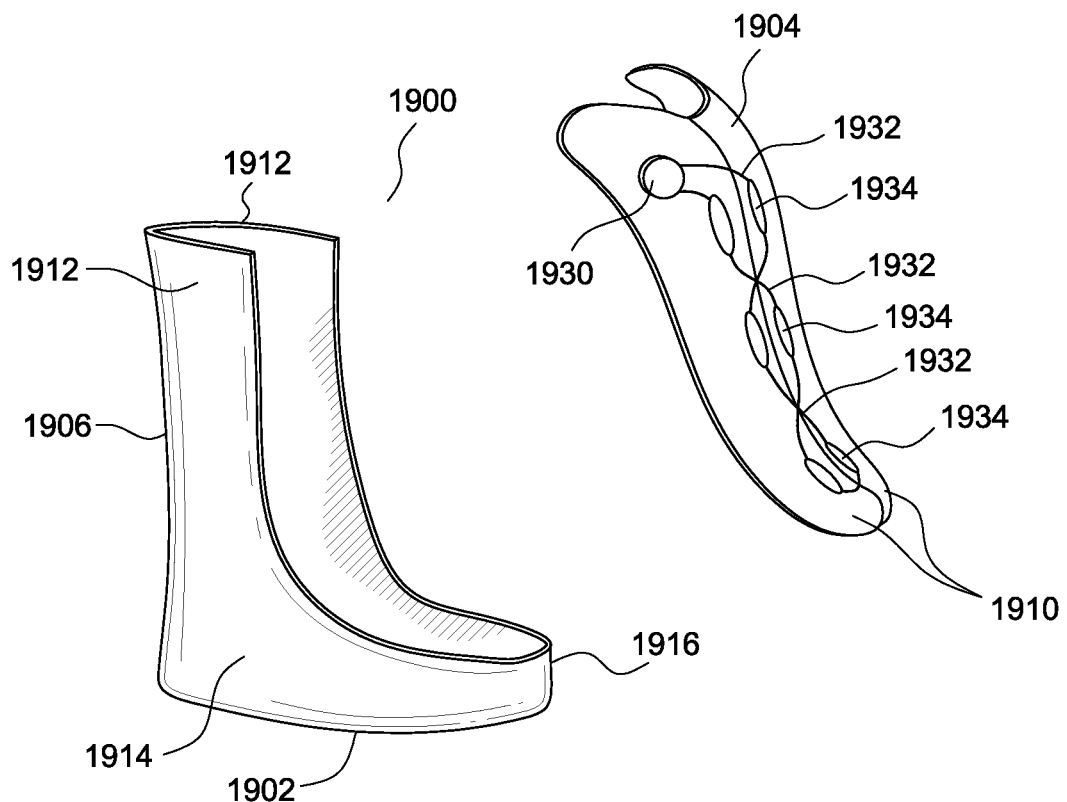
FIG. 21 represents a side perspective view of another embodiment of a circumferential walker according to the present disclosure.
Figure 22:
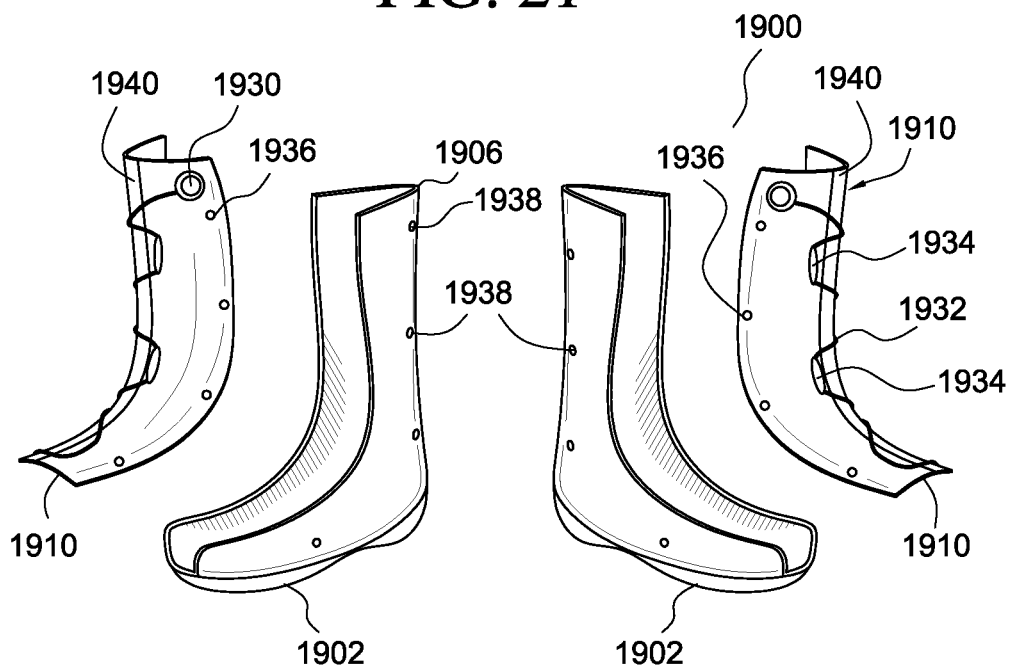
FIG. 22 represents left and right front side perspective views of a variation of the embodiment of FIG. 21.

Variations of an overlapping dorsal shell configuration walker 1900 are shown in FIGS. 21 and 22 having a similar construction, and made from similar materials as previously discussed with regard to other walker embodiments.

An outsole 1902 is attached to or integrally formed with a posterior shell 1906 having wing portions 1912, and side shell portions 1914. A toe protector portion 1916 is formed by the side shell portions 1914 extending around the anterior of the walker 1900.

Alternatively, as shown in FIG. 22, there may be no toe protector portion. Other alternatives include a toe protector portion formed integrally depending from a dorsal shell portion.

As shown in FIGS. 21 and 22, a dorsal shell 1904 is configured to correspond to the dorsal aspects of the lower leg, ankle, and foot, and to overlap the wing and side shell portions 1912, 1914. The dorsal shell 1904 is formed of at least two overlapping dorsal shell portions 1910. Variations can include multiple overlapping shell portions that correspond to the dorsal surface of the shin and the foot respectively, for example. In such a variation, four dorsal shell portions would overlap.

The overlapping dorsal shell portions 1910 can be attached to each other via a flexible fabric or material 1940, or via a releasable connection method as previously discussed. A tightening mechanism 1930 is carried on one of the overlapping dorsal shell portions 1910 near the proximal end of the anterior surface thereof. Opposed retainers 1934 are positioned on each of the overlapping dorsal shell portions 1910 and a cable 1932 is strung between the retainers 1934 and connected to the tightening mechanism as discussed above. In a variation, the connector 1940 can be eliminated, and connection between the overlapping dorsal shells 1910 can be achieved solely via the cable 1932, retainers 1934, and tightening mechanism 1930.

The dorsal shell 1904 can be removably attached to the posterior shell wing portions 1912 in any manner previously discussed. For example, each of the overlapping dorsal shells 1910 can carry connector portions 1936 thereon, which can be selectively engaged with received portions 1938 along the posterior shell wing portions 1912, and side shell portions 1914.

The method of operation of the walker 1900 is similar to previously discussed methods. The cable 1932 is first loosened, and one or both of the overlapping dorsal shells 1910 are disengaged from the posterior shell and side shells 1912, 1914 so that one of the shells 1910 can be flipped away from the opening or the dorsal shell 1904 can be completely removed from the opening. Thus, the lower leg can be inserted into the walker 1900 with ease.

Once the lower leg is placed within the walker, the detached dorsal shell portions 1910 are reattached to the posterior shell and side shells 1912, 1914, and the tightening mechanism 1930 is manipulated in order take up the cable 1932. Thus, the walker 1900 is easily tightened around the lower leg to provide suitable support and stabilization, without the use of numerous and time consuming straps.

Further variations of circumferential walkers are discussed next.

L. Detailed Description of a Strap and Dial Tensioning Configuration Walker

Figure 23:
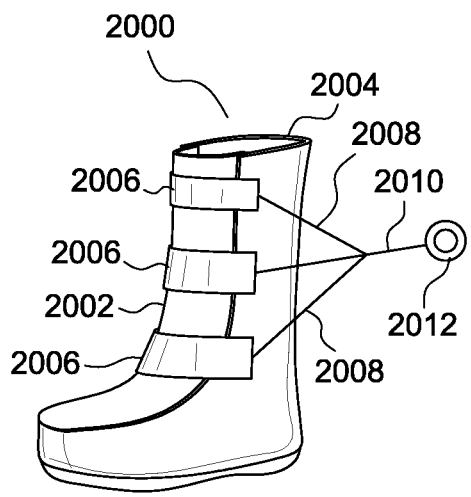
FIG. 23 is a side perspective view of another embodiment of a circumferential walker according to the present disclosure.
Figure 24:
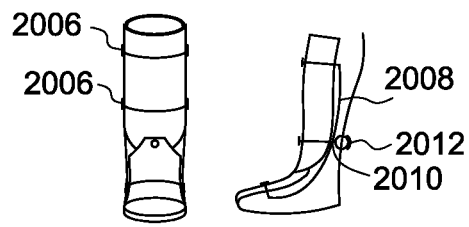
FIG. 24 represents front and side views of a variation of the circumferential walker shown in FIG. 23.
Figure 25:
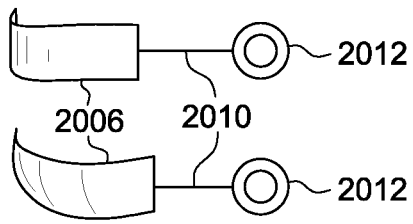
FIG. 25 illustrates a further variation of a strap configuration for use with the circumferential walker shown in FIG. 23.

As shown in FIGS. 23-25, an embodiment of a circumferential walker utilizes a strap and dial tensioning configuration in order to achieve quick and comfortable tightening of the walker around the lower leg, ankle, and foot.

As shown in FIG. 23, the walker 2000 includes a dorsal shell 2002 and a posterior shell 2004 for cooperation in a clamshell manner, as previously discussed.

Straps 2006 are positioned to extend across the dorsal shell 2002. The straps 2006 can be fixed at a first end to the posterior shell 2004 along one side of the walker 2000. The opposed second end of the straps 2006 extends across the dorsal shell 2002 for engagement with a dial tensioner 2012 in any manner discussed below, such that rotation of the dial tensioner 2012 causes tightening of the straps 2006, and hence, tightening of the walker 2000.

Returning to FIG. 23, each of the straps 2006 have a cable 2008 connected to the second end thereof. The connection may be made in any suitable manner recognized by a skilled artisan, such as via a rivet or screw connection. Each of the strap cables 2008 are subsequently connected to a main cable 2010 that is taken up and loosened via the dial tensioner 2012 in a manner as discussed above.

Thus, all of the straps 2006 can be tightened simultaneously via the dial tensioner 2012 in order to provide quick and comfortable tightening of the walker around the lower leg, ankle, and foot.

As shown in FIG. 23, the dial tensioner 2012 can be detached from the posterior shell 2004 in order to aid with removal of the lower leg, ankle, and foot from the walker.

In the variation shown in FIG. 24, the dial tensioner 2012 is positioned in a distal portion of the posterior shell 2004, and cables 2008 are attached along a side of the dorsal shell 2002 at multiple attachment points, prior to combining with the main cable 2010 that is taken up and loosened by the dial tensioner 2012.

In the variation shown in FIG. 25, each strap 2006 is connected to distinct dial tensioner 2012 in order to allow individual tightening of each strap 2006, which may provide additional control for tightening the walker around the lower leg, ankle, and foot.

In a further variation, each of the straps can be connected together via a rigid or semi-rigid element positioned along the second ends thereof, and a cable can be strung between the rigid or semi-rigid element and a dial tensioner in order to provide simultaneous tensioning of the straps.

Further variations of a circumferential walker utilizing a dial tensioning mechanism are described next.

M. Detailed Description of a Hook and Cable Dial Tensioning Configuration Walker The hook and cable dial tensioning configuration walker shown in FIG. 26 utilizes a zig-zag quick lacing structure as will be described below in order to provide quick and comfortable simultaneous tightening of the walker around the lower leg, ankle, and foot.

Figure 26:
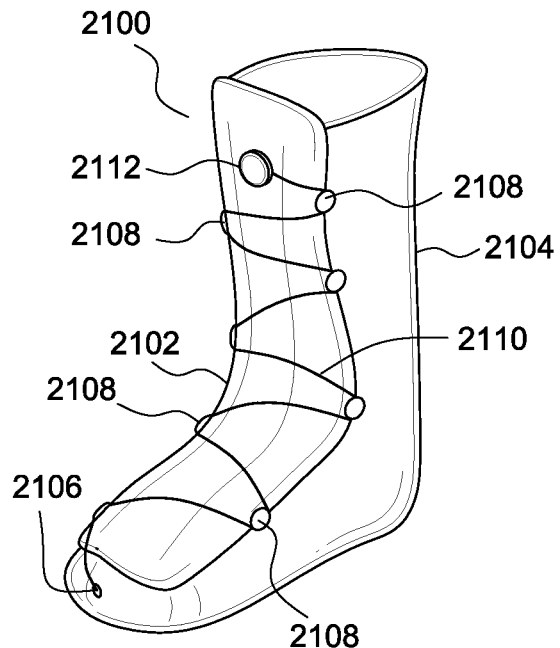
FIG. 26 is a side perspective view of another embodiment of a circumferential walker according to the present disclosure.

The walker 2100 of FIG. 26 utilizes a dorsal shell 2102 and a posterior shell 2104 that complement each other in a clamshell configuration in a manner previously discussed.

In order to provide tightening of the dorsal shell 2102 to the posterior shell 2104, a series of hooks 2108 for receiving a looped cable 2110 thereon are arranged along the edges of the posterior shell 2104 such that the cable 2110 can be looped around the hooks to create zig-zag pattern along the dorsal surface of the dorsal shell 2102.

In order to effectuate the looping of the cable 2110 around the hooks 2108, a first end of the cable 2110 is anchored at anchor point 2106 to a portion of the posterior shell 2104, for example, along the toe protector portion. The second end of the cable is arranged to be taken up or loosened via a dial tensioner 2112 that is detachably mounted to a portion of the dorsal surface of the dorsal shell 2012, for example, the proximal portion.

With the dial tensioner 2112 detached from the walker, the cable 2110 can be alternately strung between opposed hooks 2108 on opposite sides of the posterior shell 2104. Once the cable 2110 has been strung among all or some of the hooks 2108, the dial tensioner 2112 can be attached to the walker and tightened in order to simultaneously tighten all portions of the walker around the lower leg, ankle, and foot.

In this configuration, a cable can be quickly laced up along the dorsal shell 2102, and quickly tightened so that the walker provides the appropriate amount of support and stability to the lower leg, ankle, and foot.

In a variation, the cable 2110 can be looped around the posterior portion of the posterior shell in place of, or in addition to, looping the cable over the hooks 2108.

Additional variations of a circumferential walker utilizing quick pull lacing structures are discussed next.

N. Detailed Description of Quick Pull Lacing Configuration Walkers

Figure 27:
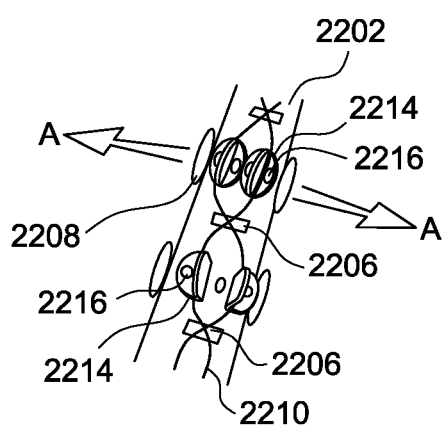
FIG. 27 is a front view of an embodiment of a dorsal shell for use with any suitable circumferential walker of the present disclosure.
Figure 28:
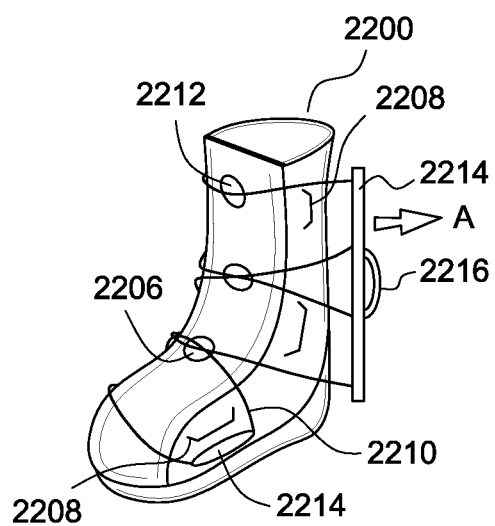
FIG. 28 is a front side perspective view of a circumferential walker utilizing a variation of the dorsal shell configuration of FIG. 27.

Variations of quick pull lacing configuration walkers are shown in FIGS. 27 and 28.

In particular, a dorsal shell 2202 for use in a circumferential walker is shown in FIG. 27. The dorsal shell 2202 is configured to cooperate with a posterior shell (not shown) in a clamshell configuration as previously discussed The dorsal shell 2202 includes retainers 2206 along the dorsal surface thereof through which a cable 2210 passes. A dial tensioner (not shown) is connected with the cable 2210 in order to tighten and loosen the cable 2210 in a manner as discussed above.

The cable 2210 is loosely strung between the retainers 2206, and connector guides 2214 are positioned along each side of the dorsal shell 2202 on the cable 2210 between the retainers 2206. The connector guides 2214 have optional finger loops 2216, through which a user can place a finger to grasp the connector guide 2214 for pulling the connector guides 2214 in the directions indicated by arrow A. The finger loops 2216 are provided as a convenience, since a user may simply grasp the connector guides 2214 themselves.

Hooks 2208 are positioned adjacent to the connector guides 2214 along the edges of the posterior shell (not shown). Each connector guide 2214 can thus be pulled in the direction A for selective engagement with a respective hook 2208. In this manner, the cable 2210 can be quick pulled and laced with the hooks 2208. Once the cable 2210 engages the hooks 2208 through the connector guides 2214, the dial tensioner can be actuated in order to tighten the cable 2210 such that the dorsal and posterior shells are drawn together.

In the variation shown in FIG. 28, the walker 2200 includes a posterior shell 2204 with multiple hooks 2208 thereon. As can be seen, the cable 2210 is strung along one side of the walker (and similarly strung on the other side) through connector guides 2214, one of which corresponds to two hook 2208 segments, the other of which corresponds to a single hook 2208. Further, a finger loop 2216 is provided on the two hook spanning connector guide, and not on the single hook connector guide. The cable is also connected to the dial tensioner 2212 for tightening and loosening in a manner previously discussed.

In this configuration, the user can more quickly quick pull lace the cable with the hooks, since multiple hooks are spanned by at least two opposed connector guides. Thus, quick pull lacing configuration provides a method for quickly and comfortably tightening a circumferential walker around the lower leg, ankle, and foot.

O. Detailed Description of Variations of a Circumferential Walker

Figure 29:
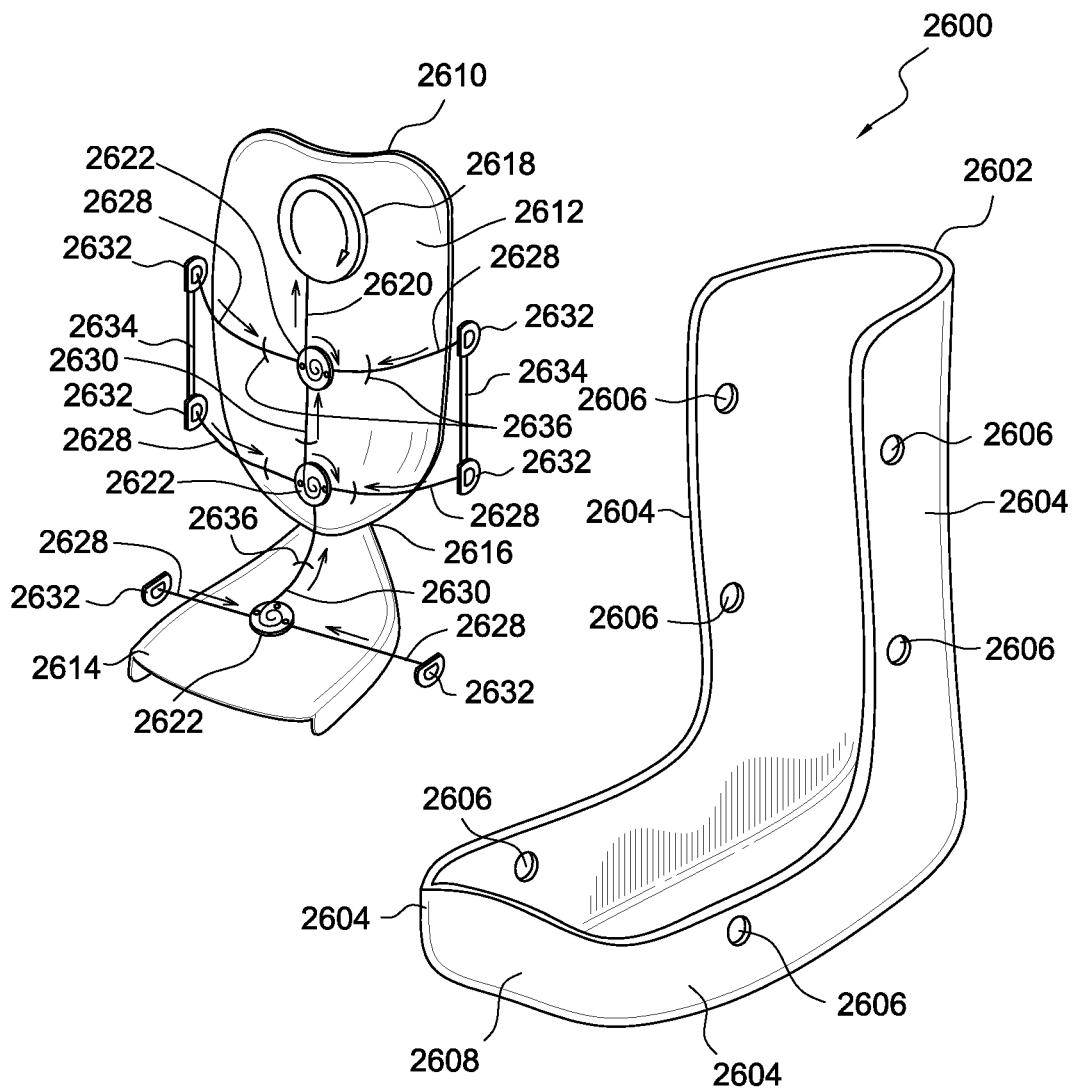
FIG. 29 is a perspective view of an embodiment of a circumferential walker utilizing a quick tensioning configuration.

As shown in FIG. 29, a circumferential, clam-shell like walker 2600 is configured in a similar manner as previously discussed. The walker 2600 includes a semi-rigid, or substantially rigid shell configuration as previously discussed.

The walker 2600 includes a posterior shell 2602 that extends from a posterior side of the lower leg and ankle, along the distal surface of the foot, and terminates in a toe cover portion 2608 that extends over the toes of a wearer to protect the toes from injury. The posterior shell 2602 includes wing portions 2604 that extend partially around the lower leg, ankle, and foot from the posterior shell 2602 to wrap around the leg in order to enclose and support the leg. Connection points 2606 are spaced along the wing portions 2604 for connecting a dorsal shell 2610 to the posterior shell in a manner to be discussed in detail below.

The dorsal shell 2610 is correspondingly shaped to the posterior shell 2602 to at least partially surround or enclose the lower leg, ankle, and foot to provide protection, support, and stabilization thereto. The dorsal shell 2610 is formed either in a single piece or in multiple shell portions. In the exemplary embodiment, the dorsal shell 2610 includes a proximal shell portion 2612 that is connected to a distal shell portion 2614 via a hinge or other suitable connection 2616.

The ease of adjusting and tightening the circumferential walker 2600 is enhanced by the use of a rotary tightening mechanism 2618 that allows each portion of the brace to be simultaneously incrementally tightened, without the need for numerous cumbersome straps. The tightening mechanism 2618 is positioned in a proximal area of the dorsal shell 2612, but can be positioned in any suitable location on the walker 2600. For example, while the tightening mechanism 2618 and the entire quick tightening arrangement are shown positioned along the dorsal shell, it will be recognized that the tightening mechanism 2618 and the quick tightening arrangement can alternatively be positioned along the posterior shell 2602.

The quick tightening arrangement will now be described in detail with respect to the configuration shown in FIG. 29. The rotary tensioning mechanism 2618 includes a main drive cable 2620 that is taken up upon a spool of the rotary tensioning mechanism 2618 via rotation of the rotary tensioning mechanism 2618 in a first direction. Rotation of the rotary tensioning mechanism 2618 in a second direction will release or unwind the main drive cable 2620 from the spool of the rotary tensioning mechanism 2618.

The main drive cable 2620 is connected to a first tensioning pulley 2622. The disclosed embodiment utilizes three tensioning pulleys 2622, but it will be recognized that more or less tensioning pulleys may be used as desired. The tensioning pulleys 2622 are spaced along the proximal and distal portions 2612, 2614 of the dorsal shell 2610. The tensioning pulleys 2622 are mounted on an axle (not shown) fixed to the dorsal shell 2610 in a manner that will be recognized by a skilled artisan so that each tensioning pulley 2622 can rotate about the axle.

Each tensioning pulley 2622 is formed from a tensioning spool 2626 with a drive spool 2624 stacked thereon. The drive spool 2624 has a smaller diameter than the diameter of the tensioning spool 2626, such that a mechanical advantage is provided to the tensioning spool 2626 via simultaneous rotation of the tensioning spool 2626 with the drive spool 2624.

As shown in FIG. 29, the second and third tensioning pulleys 2622 are respectively connected to the first tensioning pulley 2622 and each other via distal drive cables 2630. The distal drive cables 2630 are connected at a proximal end to a distal portion of the tensioning spool 2626 and at a distal end to the drive spool 2624 of the adjacent tensioning pulley 2622. Each of the drive cables 2620, 2630 has a predetermined length of cable pre-wound around the drive spool 2624 of the tensioning pulley 2622 such that tension applied to the drive cables 2620, 2630 unwinds the drive cables 2620, 2630 therefrom and rotates the drive spool 2624, and hence the tensioning spool 2626 and the entire tensioning pulley 2622 to provide tension to the portions of the walker 2600 as will be discussed in detail below.

As also shown in FIG. 29, each tensioning spool 2626 has medial-lateral tensioning cables 2628 connected at respective medial and lateral sides of the tensioning spool 2626. The medial-lateral tensioning cables 2628 are connected at a first end to the tensioning spool 2626 and at a second end to a cable connector 2632 configured to be selectively engaged and disengaged with the connection points 2606 along the posterior shell 2602 in any suitable manner, such as key slot, snap fitting, hook and loop fasteners, snap fasteners, or any other suitable connection mechanism.

As shown in FIG. 29, cable guides 2636 can be positioned along the surface of the dorsal shell 2610 to retain the drive and tensioning cables therein to prevent binding of the cables with the components of the quick tightening arrangement or other objects.

As also shown in FIG. 29, tension distributors 2634 can be utilized between the medial-lateral tensioning cables 2628 of adjacent tensioning pulleys 2622 to spread the tension of the cables along a greater surface of the posterior shell 2602 to prevent a concentration of the tension at specific points on the posterior shell 2602. The tension distributors 2634 can be a single cable spanning between adjacent tensioning pulleys 2622, or can be formed from an additional cable or element spanning only between the adjacent cable connectors 2632.

The structural configuration of the circumferential walker 2600 and the quick tensioning arrangement described above function in the following manner. Initially, the dorsal and posterior shells 2610, 2602 are either separated or connected at the connection points 2606 along only a lateral or medial side of the walker 2600 so that a wearer can place their foot, ankle, and lower leg within the posterior shell 2602 of the walker 2600. Alternatively, enough slack in the tensioning cables can be provided such that a wearer can place their foot, ankle, and lower leg within the walker 2600 when the dorsal and posterior shells 2610, 2602 are connected at the connection points 2606 along both the lateral and medial sides of the walker 2600.

Once the wearer has placed their lower limb within the walker 2600, if not already connected, the cable connectors 2632 are connected to the connection points 2606 on the posterior shell 2602. Once the dorsal shell 2610 is connected to the posterior shell 2602, the walker 2600 can be quickly tightened around the lower leg, ankle, and foot, to provide quick adjustment of the support and stabilization provided to the lower leg, ankle, and foot.

As discussed above, each of the drive cables 2620, 2630 has a predetermined length of cable pre-wound about the drive spool 2624 of the tensioning pulley 2622. Rotation of the single rotary tensioning mechanism 2618 causes rotation of each tensioning pulley 2622 via the unwinding of the drive cables 2620, 2630 from the drive spools 2624, and the subsequent winding of the drive cables 2620, 2630 upon the tensioning spools 2626 of the adjacent tensioning pulley. In this manner, the single rotary tensioning mechanism 2618 can be used to apply tension to the various portions of the walker 2600 simultaneously.

As each tensioning pulley 2622 is rotated by its respective drive cable 2620, 2630, the tensioning spool 2626 is also rotated such that the medial-lateral tensioning cables 2628 are also wound around the tensioning spool 2626 of the respective tensioning pulleys 2622. In this manner, the tension provided via the rotation of the single rotary tensioning mechanism 2618 is translated into simultaneous tensioning of numerous drive and medial-lateral cables 2620, 2630, 2628 for simultaneous tightening and adjustment of the entire walker 2600 about the lower leg, ankle, and foot. Thus, a quick and easy tightening arrangement is provided that allows the simultaneous tightening of each portion of the walker 2600 utilizing only a single rotary tensioning mechanism 2618 that can be positioned for easy manipulation by a wearer.

It will be recognized that when the rotary tensioning mechanism 2618 is rotated in a second direction to unwind the drive cable 2620 therefrom, the tension in the medial-lateral cables 2628 and the additional drive cables 2630 will cause the tensioning pulleys 2622 to rotate back to their original starting position in order to release tension to the walker 2600. Additionally, a biasing element, such as a rotary spring, can be provided to each tensioning pulley 2622 to bias the tensioning pulleys 2622 towards an initial, un-rotated position, such that a release of tension from the main drive cable 2620 will allow the tensioning pulleys 2622 to rotate back to an original position to remove the tension from the walker 2600.

Figure 30:
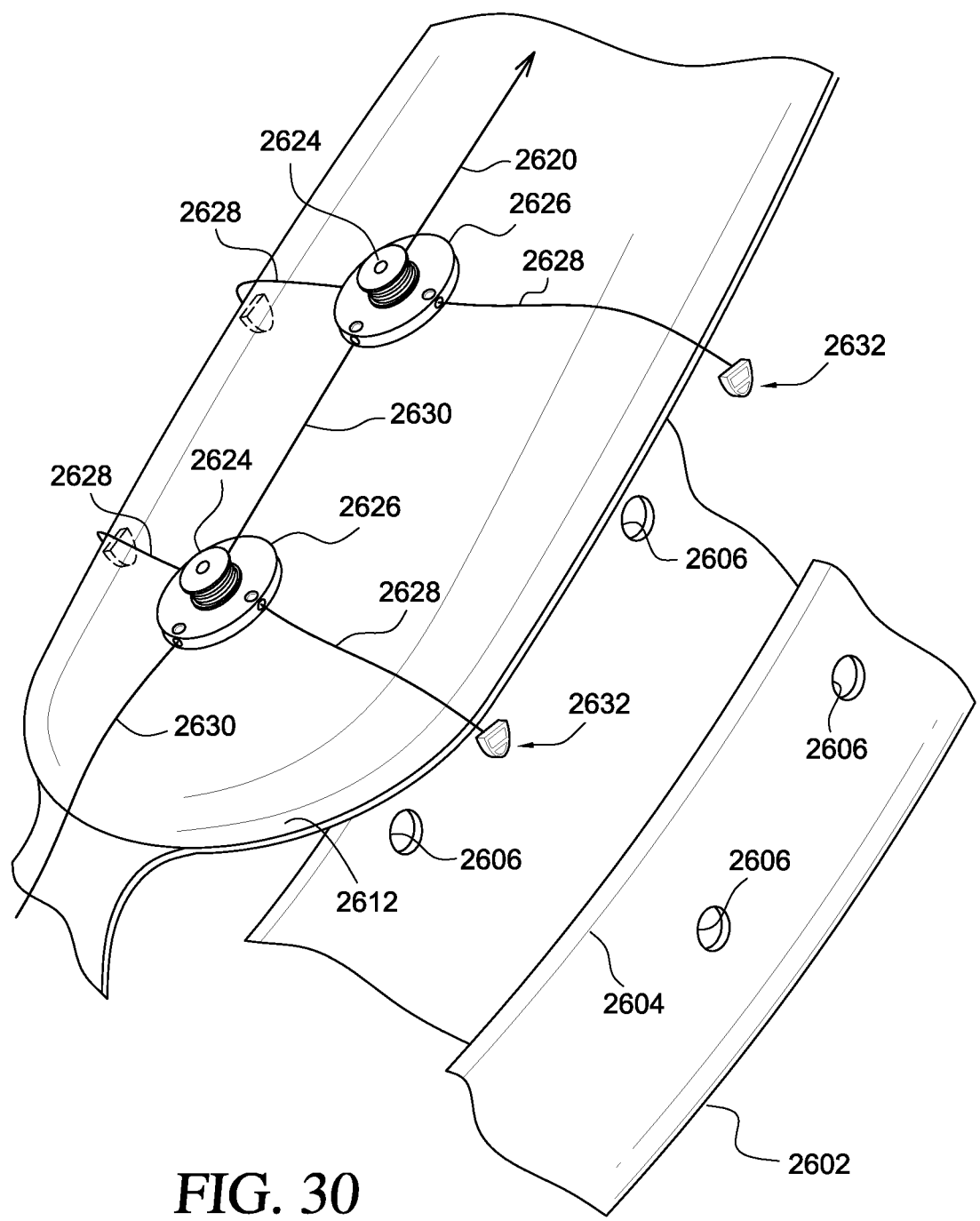
FIG. 30 is a close up, partial perspective view of a variation of the embodiment of FIG. 29.

In the variation shown in FIG. 30, the quick tensioning arrangement is similar to that shown in FIG. 29, and functions in the same manner, with the exception that there are no tension distributors used. The illustration of FIG. 30 more clearly shows how each drive cable 2620, 2630 has a predetermined length pre-wound about the drive spool 2624.

Figure 31:
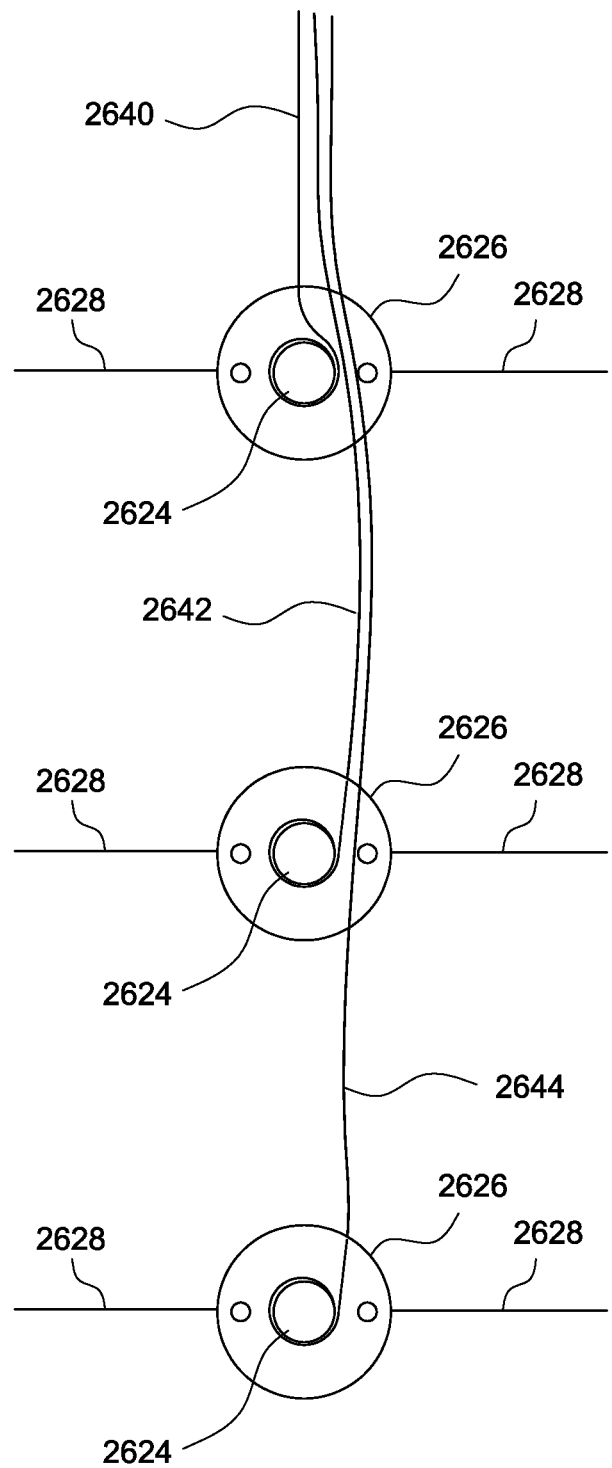
FIG. 31 is a close up partial view of a variation of a quick tensioning arrangement for use with the circumferential walker shown in FIG. 29.

In the variation shown in FIG. 31, which functions in the same manner as described above, first, second, and third drive cables 2640, 2642, 2644 are respectively connected at one end to the rotary tensioning mechanism 2618 and at the other end to a respective drive spool 2624 of a tensioning pulley 2622.

As with the drive cables discussed above, first, second, and third drive cables 2640, 2642, 2644 have a predetermined length wound about the drive spool 2624 of a respective tensioning pulley 2622 such that rotation of the rotary tightening mechanism 2618 causes the tensioning pulleys 2622 to rotate to wind the medial-lateral tensioning cables 2628 thereon to provide tension to portions of the walker 2600 simultaneously.

Figure 32:
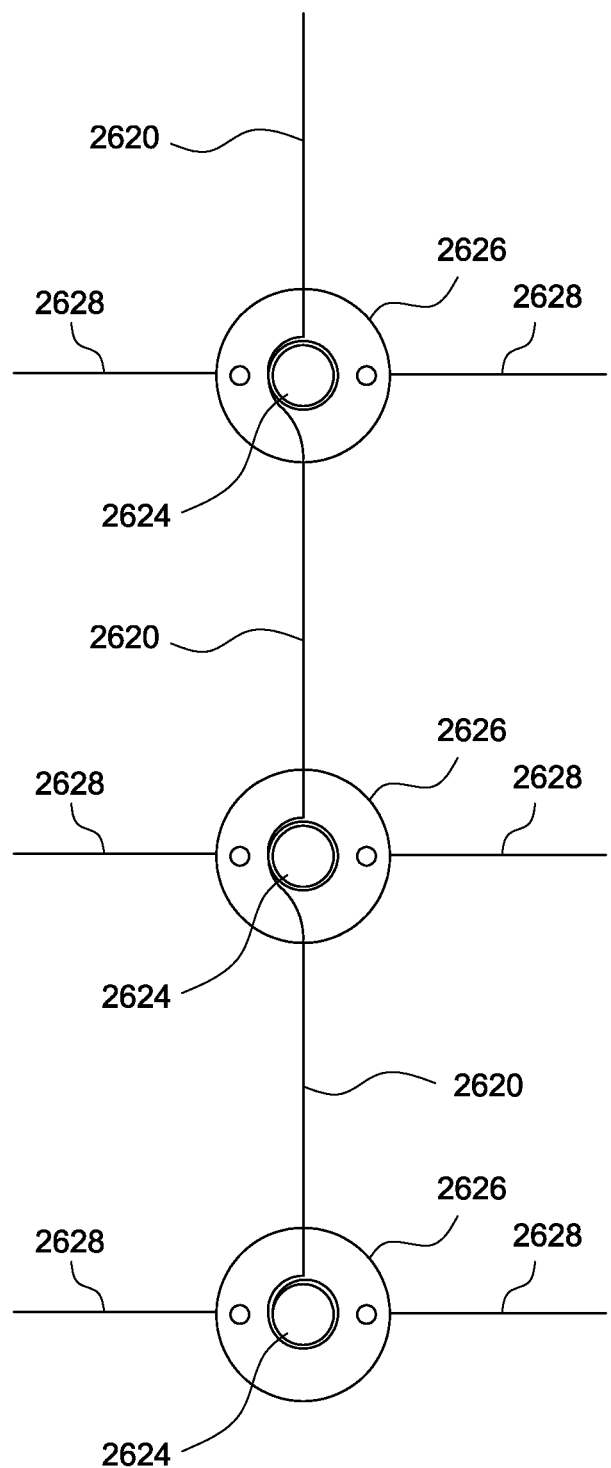
FIG. 32 is a close up partial view of a variation of a quick tensioning arrangement for use with the circumferential walker shown in FIG. 29.
Figure 38:
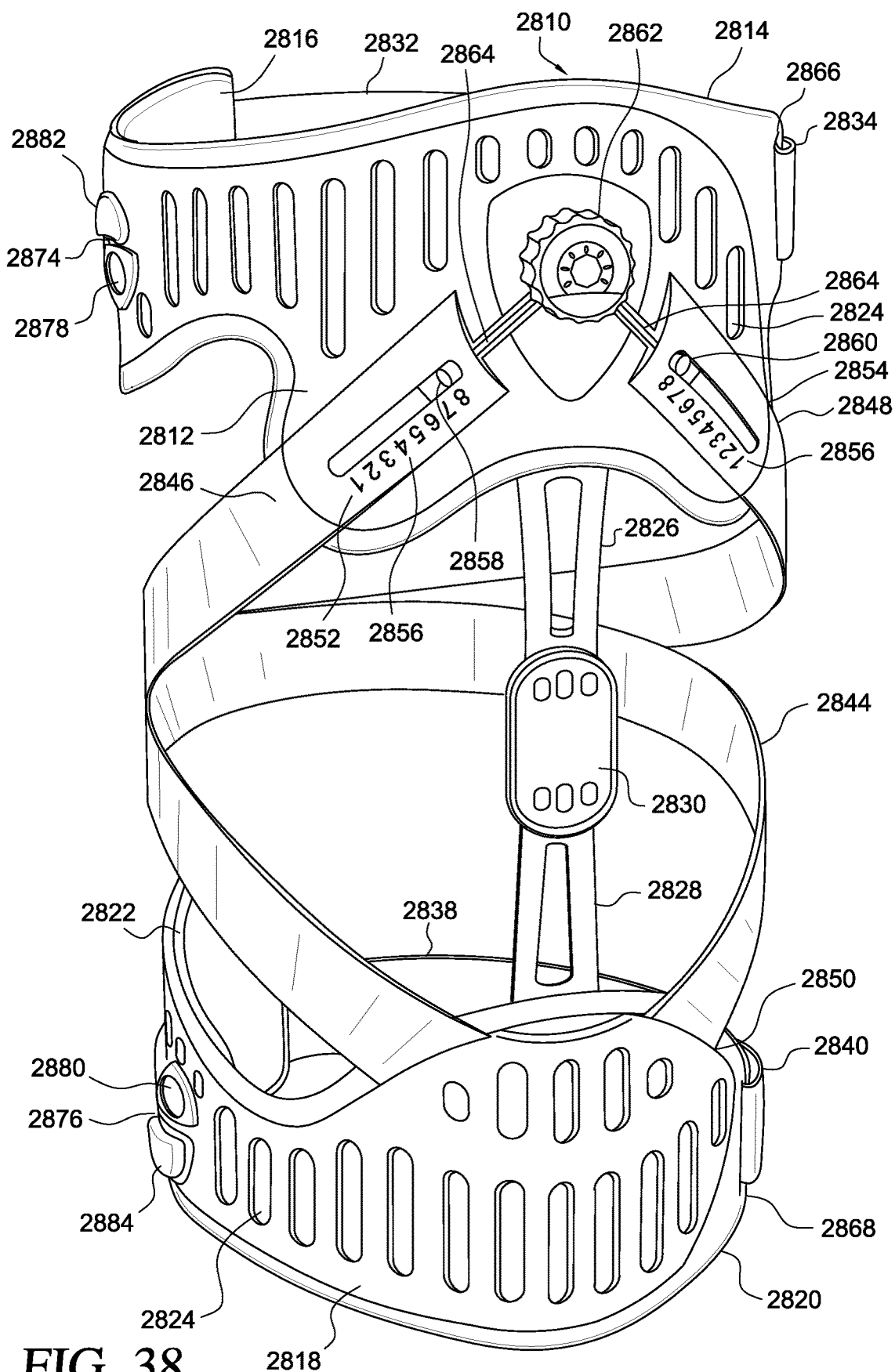
FIG. 38 is a front side perspective view of an embodiment of a knee brace according to the present disclosure.
Figure 39:
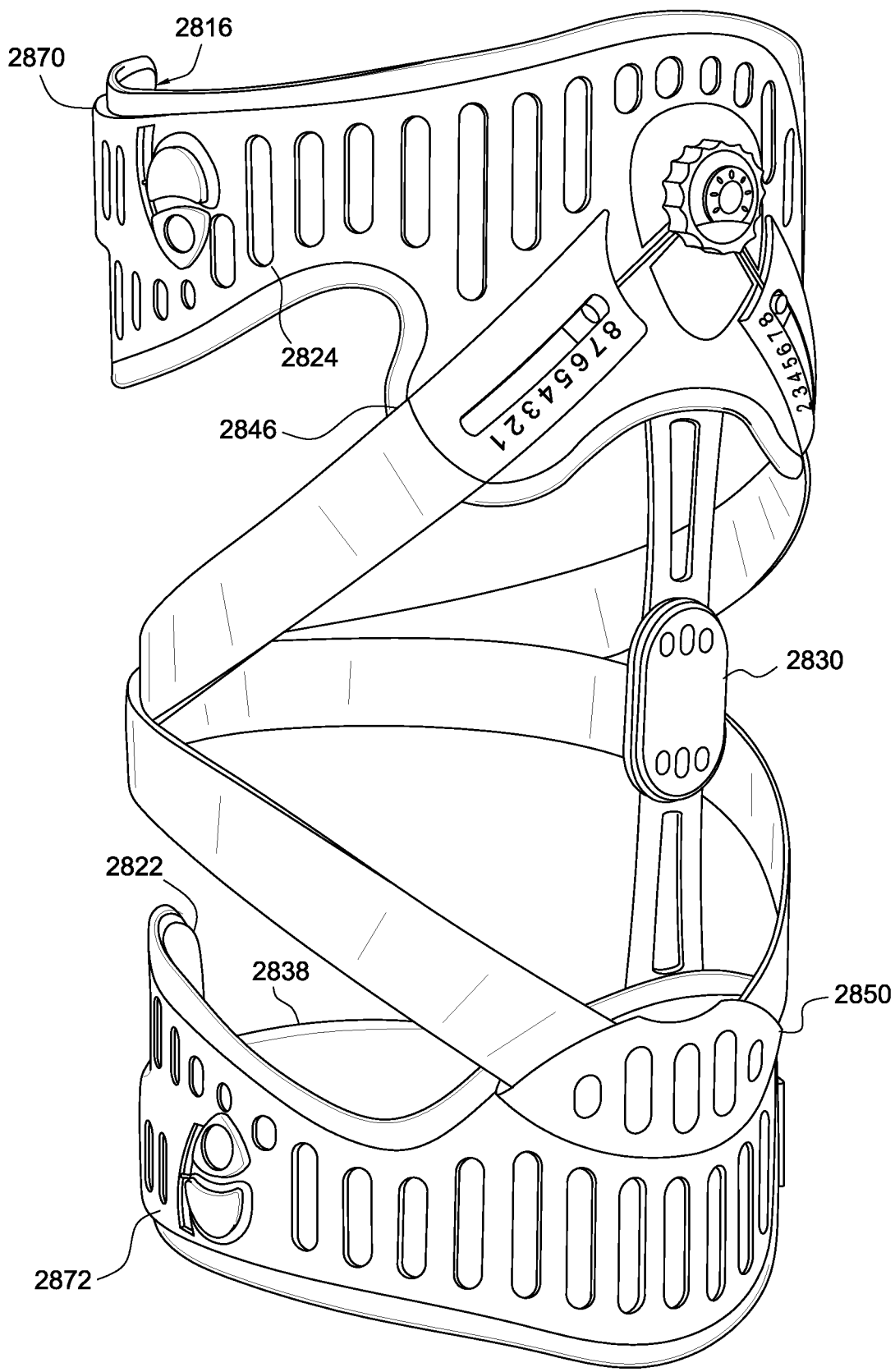
FIG. 39 is a further front side perspective view of the knee brace of FIG. 38.

In a further variation, shown in FIG. 32, a single main drive cable 2620 is connected between the rotary tightening mechanism 2618 and the drive spool 2624 of each tensioning pulley 2622. The drive cable 2620 can be anchored at one end to the most distal tensioning pulley 2622. A predetermined length of the drive cable is then wound around the drive spool 2624 of the most distal tensioning pulley 2622. The drive cable 2620 is then strung to the next tensioning pulley 2622 and a predetermined length thereof is wound around the drive spool 2624 thereof. This is repeated until the second end of the drive cable 2620 is connected to the rotary tightening mechanism 2618.

Rotation of the rotary tightening mechanism 2618 thus causes simultaneous rotation of each tensioning pulley 2622 via the friction between the drive cable 2620 and the wound portion thereof about each drive spool 2624.

P. Detailed Description of Variations of Pulleys for Use with a Circumferential Walker Variations of tensioning pulleys for use with the circumferential walker discussed above are shown in FIGS. 33-37. The general function of the variations of quick tightening arrangements are similar to that previously discussed and the focus of the following discussion is on the particular configuration of various tensioning pulleys that can be used with the previously described quick tightening arrangements of a circumferential walker.

A first variation of a pulley for use with the embodiments shown in FIGS. 29-31 is shown in FIG. 33. The tensioning pulley 2660 shown in FIG. 33 is formed of first and second stacked plates 2662, 2664 having four cable anchors 2666 positioned therebetween at opposed proximal-distal and medial-lateral positions.

For purposes of discussion, the tensioning pulley 2660 is the closest pulley to the rotary tensioning mechanism and a main drive cable 2668 is pre-wound around the four cable anchors 2666 such that rotation of the rotary tensioning mechanism causes simultaneous rotation of the tensioning pulley 2660 in the manner previously discussed.

An additional drive cable 2672 is connected at a first end to the distal cable anchor 2666 and is pre-wound at a second end to an adjacent tensioning pulley 2660 in the same manner as the main drive cable 2668 as just discussed for simultaneous rotation of each tensioning pulley 2660 with the rotation of a rotary tensioning mechanism.

Further, medial-lateral tensioning cables 2670 are connected at a first end to the medial and lateral cable anchors 2666 such that rotation of the tensioning pulley 2660 causes the medial-lateral tensioning cables 2670 to be wound around the cable anchors 2666 to provide simultaneous tightening of the walker in a manner previously discussed.

The configuration of the tensioning pulley 2660 can provide a low profile pulley that does not include a protruding drive spool that may inadvertently catch on objects, thus providing an improved low profile circumferential walker.

The remaining variations of tensioning pulleys shown in FIGS. 34-37 are suitable for use with the embodiment shown in FIG. 32, which utilizes a single main drive cable spanning between the rotary tensioning mechanism and each adjacent tensioning spool. Whereas the embodiment of FIG. 32 relies solely on the friction between the drive cable and the drive spool of the tensioning pulley to provide the rotation thereof, the embodiments of FIGS. 34-37 provide a mechanism to ensure mechanical transfer of forces between the main drive cable and the tensioning pulleys.

For example, as shown in FIG. 34, a tensioning pulley 2650 includes a main drive cable 2652 that extends through a main drive cable guide 2654 formed in the tensioning pulley 2650. The main drive cable 2652 extends through the cable guide 2654 and is subsequently pre-wound about the tensioning pulley 2650 as previously discussed. Since the main drive cable 2652 extends through the cable guide 2654, as the drive cable 2652 is tensioned via rotation of the rotary tensioning mechanism, the drive cable 2652 will be mechanically "locked" to the tensioning pulley 2650 to cause corresponding rotation thereof.

Similarly, as shown in FIG. 35, a tensioning pulley 2680 includes first and second spaced plates 2682, 2684 that have a main cable anchor 2686 centrally positioned therein and medial-lateral cable anchors 2690 positioned at medial and lateral portions thereof. A main drive cable 2688 extends through, and has a predetermined length pre-wound upon, the main cable anchor 2686 to provide rotation of the tensioning pulley 2680 in a manner discussed above. Medial-lateral cables 2692 are anchored to the medial-lateral cable anchors 2690.

Similarly to the tensioning pulley shown in FIG. 34, the tensioning pulley 2680 provides a mechanical "lock" between the drive cable 2688 and the tensioning pulley 2680 to ensure rotation thereof via tensioning of the drive cable 2688.

In a further variation shown in FIG. 36, a tensioning pulley 2700 has a guide slot 2704 passing therethrough to guide and retain the main drive cable 2702 therein. Medial-lateral cable anchors 2706 are provided thereon to anchor medial-lateral tensioning cables 2708. The drive cable 2702 passes through the guide slot 2704 and is wound around the tensioning pulley 2700. Thus, in accordance with previously discussed variations, a mechanical "lock" occurs between the drive cable 2702 and the tensioning pulley 2700.

The tensioning pulley 2700 can have an oblong or elliptical shape in the proximal-distal direction to provide a mechanical advantage between rotation of the main drive cable 2702 and the medial-lateral tensioning cables 2708.

The variation of a tensioning pulley 2710 shown in FIG. 37 is similar to that of the variation shown in FIG. 8 and includes a guide slot 2714 passing therethrough to guide and retain the main drive cable 2712 therein. Medial-lateral cable anchors 2716 are provided thereon to anchor medial-lateral tensioning cables 2718. The drive cable 2712 passes through the guide slot 2714 and is wound around the tensioning pulley 2710. Thus, in accordance with previously discussed variations, a mechanical "lock" occurs between the drive cable 2712 and the tensioning pulley 2710.

The tensioning pulley 2710 can have an oblong or elliptical shape in the medial-lateral direction to provide a mechanical advantage between rotation of the main drive cable 2712 and the medial-lateral tensioning cables 2718.

Q. Other Orthopedic Devices Having Rotary Ratcheting

The features of the aforementioned circumferential walker and the description in U.S. Pat. No. 7,198,610 may be extended to a variety of other orthopedic devices.

For example, a wrist brace having a strapping system such as those described in U.S. Pat. No. 7,311,686 and U.S. patent application publication 2007/0239093, incorporated by reference and commonly owned by the assignee of this application, may include a rotary tensioning device. For example, a rotary ratchet of the type described in U.S. Pat. No. 7,198,610 may be combined with an individual strap such that a cable and a rotary ratchet or dial tensioner to connect to the strap to enable incremental unidirectional adjustment of the wrist brace.

In a variation, the wrist brace may be arranged with a plurality of retainers or hooks located on opposed sides of the wrist brace panels, and a cable is laced through and about such retainers or hooks and coupled to a dial tensioner to draw the sides of the wrist brace to one another. A middle panel or dorsal shell may be provided much in the same manner as in the circumferential walker described above. The wrist brace may be arranged similarly to the embodiments described in connection with at least FIGS. 13 and 20 provided herein. In another variation, the plurality of straps may be connected to one another by a cable which is coupled to a dial tensioner, much in the form of the embodiment described in connection with FIGS. 23-25 provided herein.

Another example of an orthopedic device is an ankle brace described in U.S. Pat. No. 7,311,686. The ankle brace of the U.S. Pat. No. 7,311,686 may be modified in that the laces can be replaced with a dial tensioner arrangement in connection with the embodiments of FIGS. 13, 20 26 provided herein. Other suitable arrangements may be used to replace the laces and strapping of the ankle brace which are consistent with the dial tensioner embodiments described and incorporated herein.

Yet another example of an orthopedic device is a knee brace having circumferential or partial circumferential straps. An example of one type of a knee brace is described in U.S. Pat. No. 7,037,287, and another type of a knee brace is depicted in U.S. Pat. No. D558,884, both of which are incorporated by reference herein and commonly owned by the assignee of this application. These straps may be individually connected to a dial tensioner much in a manner described in U.S. Pat. No. 7,198,610, or a series of the straps may be connected to a dial tensioner much in a manner described in FIG. 23. Similarly, other braces, such as elbow and back braces may include similar dial tensioner arrangements as in the knee brace.

In yet another example of an orthopedic device is a cervical collar of the type described in U.S. Pat. Nos. 6,254,560 and 6,921,376 which are incorporated herein by reference and commonly owned by the assignee of this application. In the cervical collar, a single dial tensioner may be coupled to or replace a circumferential strap or straps which retain the cervical collar on the patient. The dial tensioner can advantageously permit incremental adjustment at low increments to allow for gradual and sensitive adjustment of the tightness of straps or cables retaining the collar on the patient.

In a variation of the cervical collar, one end of a strap or opposed ends of a strap may be coupled to a cable connected to a dial tensioner. In another variation, the dial tensioner may be of any of the types described herein and the cervical collar can be arranged such that parts of the collar are drawn together by a plurality of cables, such as in the embodiments of FIGS. 16, 19, 23 and 26.

R. Detailed Description of a Knee Brace

As discussed above, the embodiment of the knee brace disclosed herein may be of an unloading, osteoarthritic knee brace of a type generally described in U.S. Pat. No. 7,198,610. Accordingly, the description herein focuses on the structure, materials, and configuration of a particular embodiment of an unloading, osteoarthritic knee brace, without belaboring the particular effects and modalities for treating osteoarthritis in the knee joint.

Referring to FIGS. 38-42, an embodiment of an orthopedic device is illustrated in the form of a knee brace 2810 suitable for stabilizing, protecting, supporting, unloading, and/or rehabilitating the knee. As shown, the knee brace 2810 is composed of proximal and distal shells 2812, 2818 that are connected to each other via proximal and distal supports 2826, 2828 that engage a flexion-extension hinge 2830 for rotation thereabout in a manner that will be recognized by a skilled artisan.

Suitable materials for use as proximal and distal shells 2812, 2818, the proximal and distal supports 2826, 2828, and the hinge 2830 may include plastics, carbon or glass fiber and epoxy composites, metals, such as aluminum, or any other suitable material. It will be recognized that different materials may be used for each of the components.

As shown in FIGS. 38-42, the proximal and distal shells 2812, 2818 each include a main portion that extends along the lateral side of the knee brace 2810 and a substantially horizontally extending arcuate portion configured to extend around the anterior portion of the leg, and around the medial side of the leg. The proximal and distal shells 2812, 2818 are suitably formed of a material that provides support to the knee joint and leg, while being flexible enough to allow the proximal and distal shells 2812, 2818 and the horizontally extending arcuate portions to conform to the geometry of the leg and knee joint of the user. It is understood that composite materials, plastics, such as polyethylene, or metals, such as aluminum, are materials suitable to achieving support for the knee joint and leg while providing suitable flexibility.

In order to provide ventilation for the user when the knee brace 2810 is secured to the leg, so that perspiration may evaporate therethrough, slots or openings 2824 are defined within the proximal and distal shells 2812, 2818. The slots or openings 2824 also reduce the weight of the knee brace 2810 by removing material therefrom and further impart flexibility to portions of the proximal and distal shells 2812, 2818.

In the embodiment shown in FIGS. 38-42, the proximal and distal shells 2812, 2818 are overall substantially flexible to allow the shells to conform to the outline of the leg. Specifically, while the proximal and distal shells 2812, 2818 should have a degree of toughness or rigidity to provide support to the leg and knee joint, as discussed above, they also are flexible enough to allow the proximal and distal shells 2812, 2818 to conform to the geometry of the leg and knee joint when suitable forces are applied, for example via strapping assemblies.

Referring to FIGS. 38-42, an additional feature of the embodiment of the knee brace 2810 that provides comfort and structures for affixing straps, as will be discussed in detail below, is the secondary, discrete regions of material integrally formed around the edges of the proximal and distal shells 2812, 2818. As previously discussed, the proximal and distal shells 2812, 2818 each include a discrete rigid, hard, and/or tough region that essentially defines a central portion along the proximal and distal shells 2812, 2818 and that is rigid and tough enough to provide support to the knee brace 2810 and the leg, yet still allows the proximal and distal shells 2812, 2818 to be substantially flexible so as to conform to the geometry of the leg and knee joint. Each of these regions has a first stiffness consistent with these features.

In addition, discrete flexible and/or elastic regions 2814 and 2820 generally surround, and are integrally formed with the respective main regions of the proximal and distal shells 2812, 2818. The discrete regions 2814, 2820 are formed so as to have less stiffness than the respective main regions. In this manner, regions 2814, 2820 essentially provide a compliant, pressure relieving interface between the harder main regions and the leg and knee joint of the user. The regions 2814, 2820 further may provide additional frictional engagement between the proximal and distal shells 2812, 2818 and the leg of the user, due to the lower stiffness of the regions 2814, 2820.

The discrete regions 2814, 2820 are distinguished from the main regions in that they preferably have a softer texture. More specifically, the discrete regions 2814, 2820 have a hardness that is lower than the hardness of the respective main regions. The two discrete regions 2814, 2820 may be integrally formed with the respective main regions using any suitable technique, such as casting, or injection molding.

According to an exemplary embodiment, the respective main regions and the discrete regions 2814, 2820 are formed from materials having different hardnesses. In this variation, the respective main regions and the discrete regions 2814, 2820 are injection molded thermoplastics that are integrally molded together. An exemplary combination of materials comprises thermoplastic polyurethane elastomers sold under the name ELASTOLLAN by BASF group.

In making the shells 2812, 2818 of this variation, the main regions are first fabricated by being formed by a first mold. A first material, such as ELASTOLLAN S60D53N, is injected into the mold so as to result in the formation of the main region of the shells 2812, 2818. The molded shells 2812, 2818 are then transferred to another, larger second mold which forms the overall finished shape of the shells 2812, 2818. The shells 2812, 2818 are secured and centered in the second mold. A second material, such as ELASTOLLAN C60A10W, is injected into the second mold so as to contact the shells 2812, 2818 and form the discrete regions 2814, 2820 therearound. Due to the similarity in composition of the first and second materials, the second material of the discrete regions 2814, 2820 bond to the first material of the main regions of the shells 2812, 2818 as it is formed in the second mold. In this variation, the first material has a hardness that is greater than the second material.

A significant advantage to this configuration is that the combination of a flexible, yet tough main region with a softer region 2814, 2820 surrounding and bordering the tough region of the shells 2812, 2818 provides a substantially comfortable feature to the orthopedic brace.

Another advantage to this variation is that the shells 2812, 2818 and the respective discrete regions 2814, 2820, may be pigmented in different colors. This results in an appearance that results in a piping around the periphery of the shells 2812, 2818 which provides a visually pleasing appearance. For example, the first material used for forming the main region of the shells 2812, 2818 may have a black pigment, whereas the second material used for forming the discrete regions 2814, 2820 may have a gray pigment.

While similar materials are described in connection with this variation, it will be noted that dissimilar materials may also be used. For example, polyethylene, polyurethane and other thermoplastics may be used for forming the main region of the shells 2812, 2818, and suitable materials such as vinyl, rubber or thermoplastic elastomers may be used for forming the discrete regions 2814, 2820. Other methods for forming the main region of the shells 2812, 2818 with the discrete regions 2814, 2820 may be found in U.S. Pat. Nos. 5,445,602 and 5,716,335, incorporated herein in the entirety by reference. Moreover, a soft flexible region may be mechanically adhered, such as by an adhesive, to a shell having ledge, slotted or groove portions upon which the flexible region may be adhered and that does not interlock with any structure of the shell.

Additional comfort may be provided by the utilization of padding or spacer elements 2816, 2822 between the shells 2812, 2818 and the leg of the user. Such padding may be ventilated, with for example holes or channels, so that perspiration may evaporate from the skin of the user. Exemplary configurations of ventilated padding are disclosed in U.S. publication no. 2006/0135900 A1 on Jun. 22, 2006, and incorporated above by reference.

In addition to the above described features, the proximal and distal shells 2812, 2818 each include appropriate structures for receiving and retaining straps of the device that are utilized to maintain the device in position on the body and to provide the appropriate amount of stability and support and/or unloading of the joint.

In particular, each of the proximal and distal shells 2812, 2818 include respective connection points 2866, 2868 and receiving portions 2870, 2872 for respectively connecting first ends 2834, 2840 of first and second 2832, 2838 stability straps and receiving respective second ends 2836, 2842 of the first and second 2832, 2838 stability straps therein.

The connection points 2866, 2868 can be formed as slots in the discrete regions 2814, 2820 and the first ends 2834, 2840 of the first and second 2832, 2838 stability straps can be looped through the slots and connected to themselves in any suitable manner, such as by hook and loop fasteners or snap fasteners.

The receiving portions 2870, 2872 can be formed in the main regions of the respective shells 2812, 2818 in a shape generally corresponding to the shape of the first and second 2832, 2838 stability straps. The second ends 2836, 2842 of the first and second 2832, 2838 stability straps are inserted into the respective receiving portions 2870, 2872.

In addition, the proximal shell 2812 includes first and second 2852, 2854 receiving portions configured to receive respective first and second ends 2846, 2848 of a force strap 2844. The first and second 2852, 2854 receiving portions can include indicia 2856 for indicating the tension in the force strap 2844, as will be discussed in detail below.

The distal shell 2818 also includes a retainer portion 2850 arranged along a proximal portion of the shell and configured for retaining a mid-section of the force strap 2844 therein. While a single force strap 2844 is disclosed spiraling around the knee brace 2810 and passing through the retainer portion 50, two distinct force straps that are respectively anchored to the knee brace 2810 can be utilized in place of the single force strap 2844.

Turning again to the arrangements provided to secure the knee brace 2810 to a user's leg and knee joint, first and second stability straps 2832, 2838 connect to the proximal and distal shells 2812, 2818 in a manner providing much versatility for accommodating many variable geometries of leg and knee joints, and in a quick tensioning manner. The stability straps 2832, 2838 are utilized to secure the proximal and distal shells to the thigh and calf portions of the leg by wrapping around the respective leg portions. The stability straps 2832, 2838 may be formed from any suitable material, such as plastic, so as to be flexible enough to wrap around and configure to the geometry of the leg and knee joint. The stability straps 2832, 2838 may be formed in any known suitable manner, such as casting or injection molding. Each of the stability straps 2832, 2838 may include a cushion feature, such as foam or a textile pad that is secured thereon for enhanced rotational prevention and additional comfort. Of course, the cushion feature may be any suitable pad, such as a ventilated pad of the type previously discussed.

Figure 41:
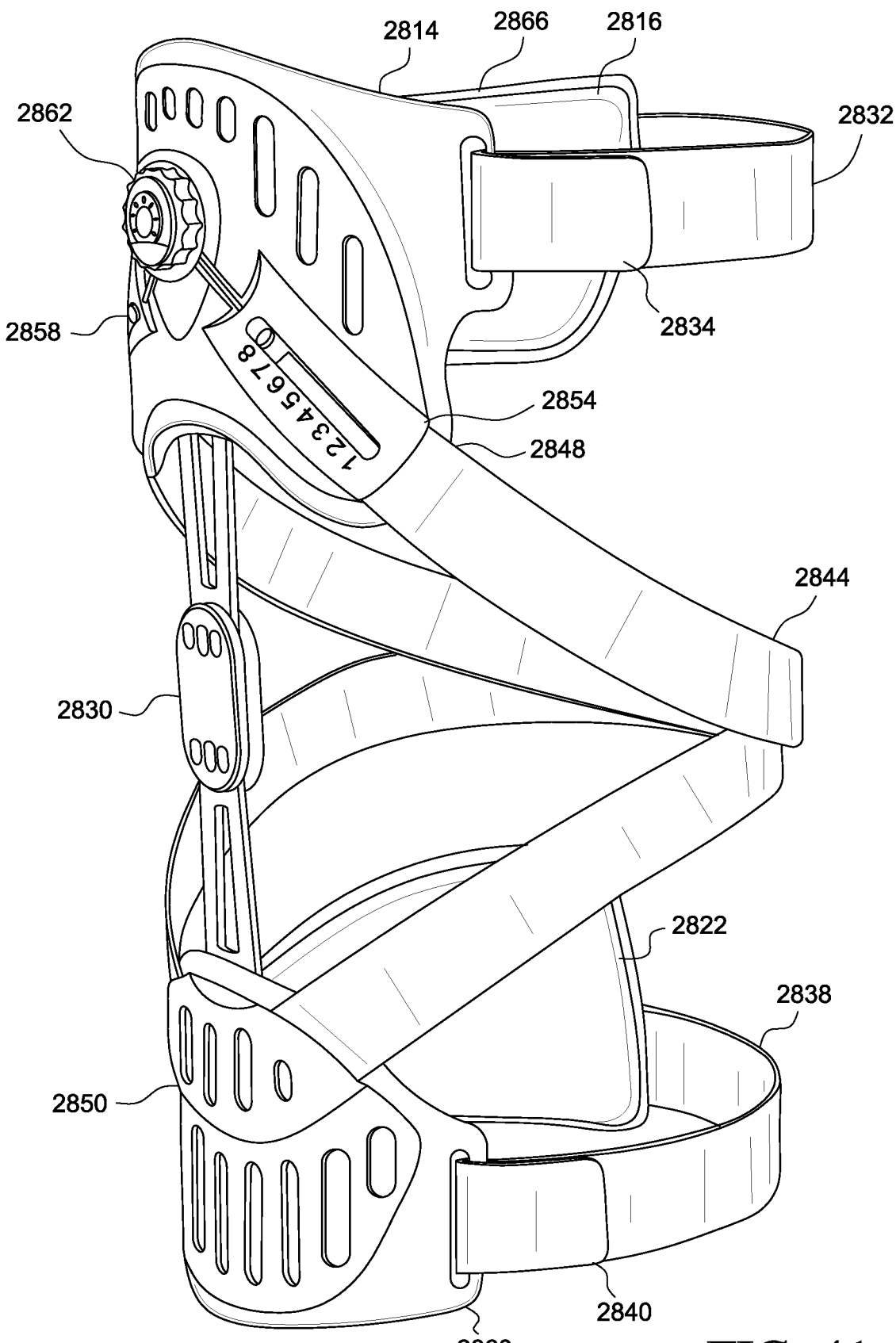
FIG. 41 is a rear side perspective view of the knee brace of FIG. 38.

As best seen in FIG. 41, and as described above, the first ends of the stability straps are connected to the shells in a manner that allows the stability straps to be selectively connected or disconnected. The first ends of the stability straps can be looped through a slot in the discrete regions of the shells (or in the shells themselves) and connected to the straps themselves via suitable mechanisms, such as hook and loop or snap fasteners. Thus, the stability straps can be adjusted. The straps can further be adjusted utilizing pull tightening mechanisms 2874, 2876.

Figure 40:
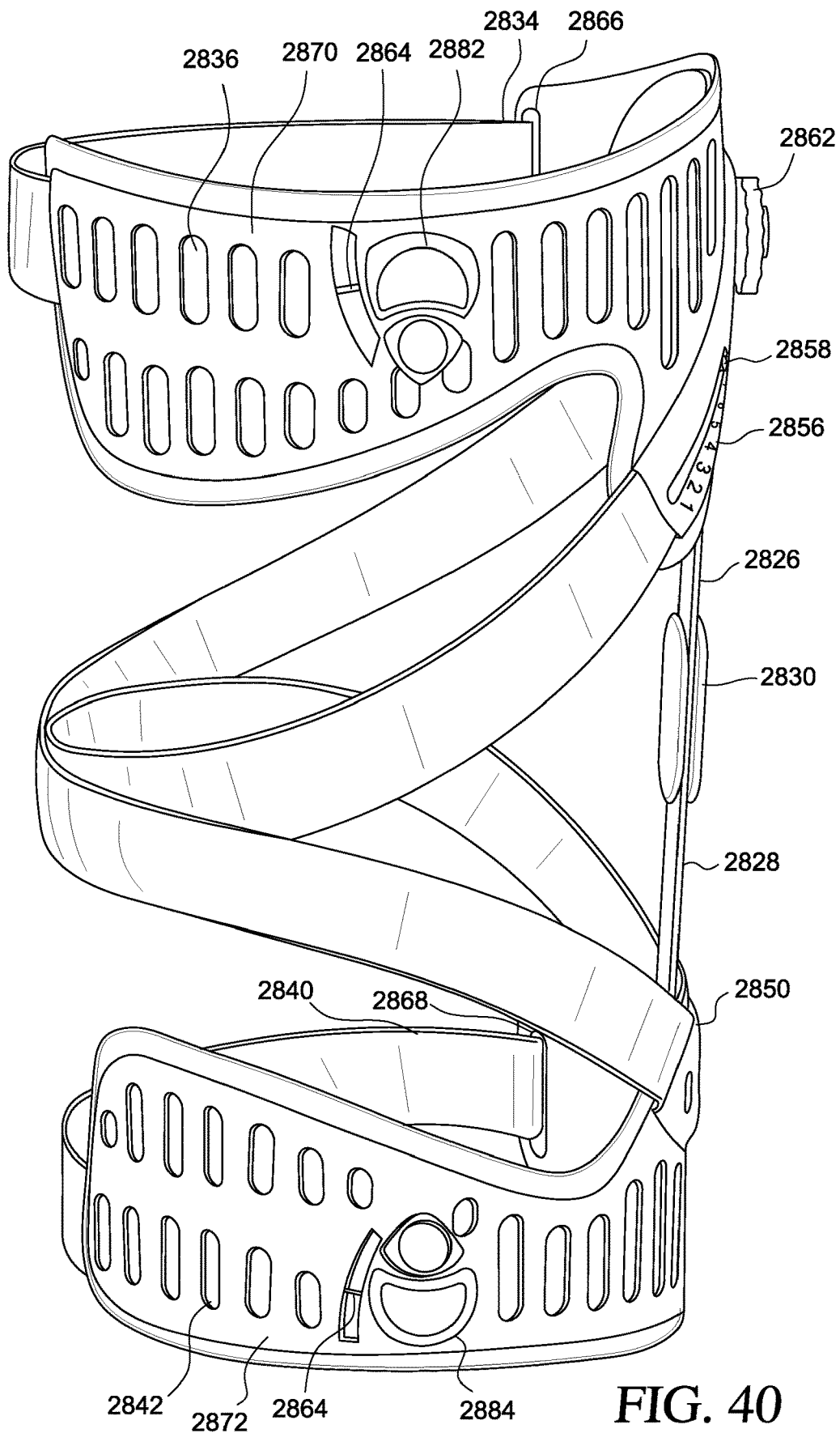
FIG. 40 is a front perspective view of the knee brace of FIG. 38.
Figure 42:
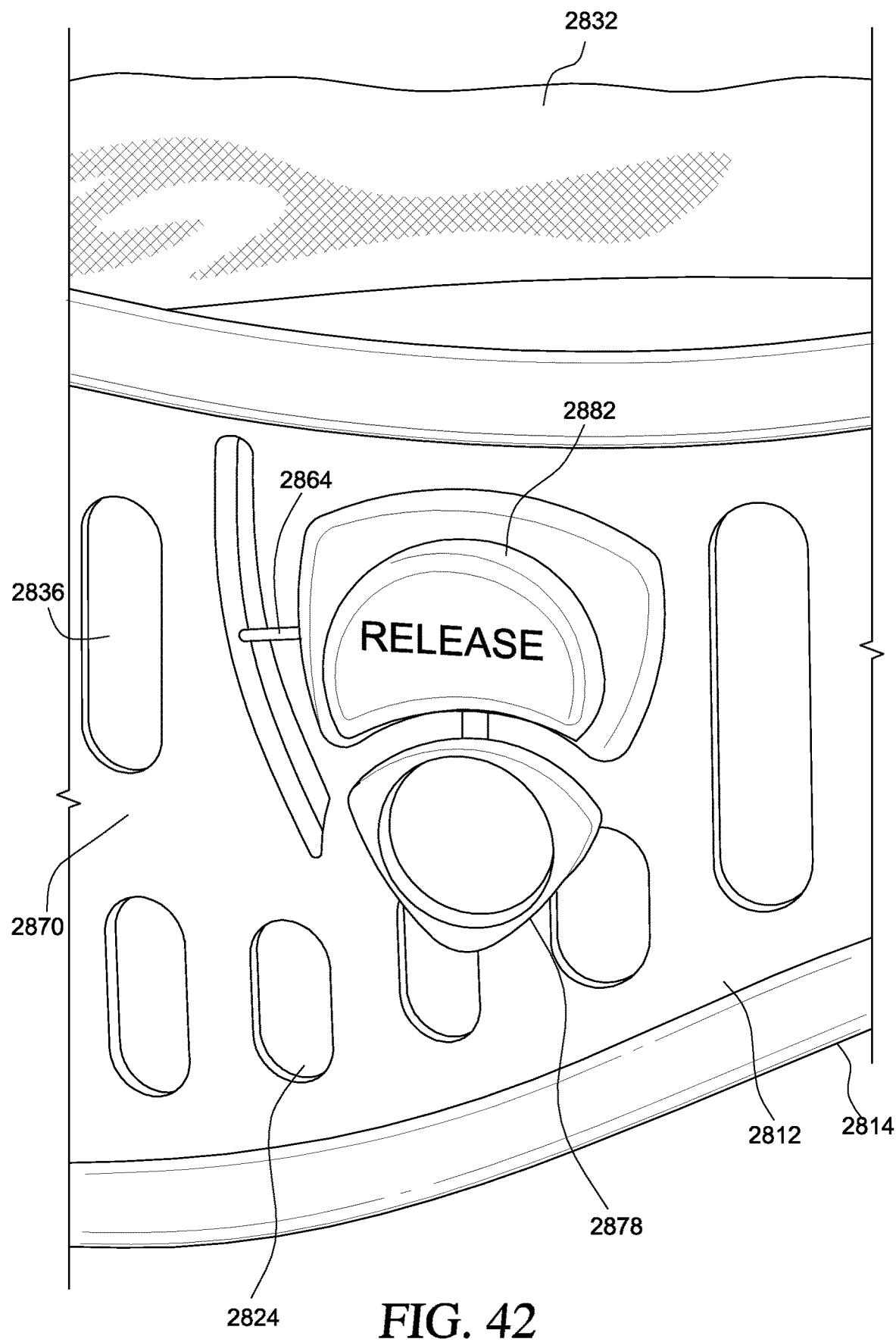
FIG. 42 is a magnified perspective view of a pull assembly of the knee brace of FIG. 38.

As best seen in FIGS. 40 and 42, pull tightening mechanisms 2874, 2876 are engaged with the second ends 2836, 2842 of the stability straps via end connectors (hidden from view, see end connectors 2858, 2860 described below) and a cable or lace 2864. The cable 2864 is fed through respective release mechanisms 2882, 2884 and connected with respective pull tabs 2878, 2880.

The release mechanisms 2882, 2884 may include a locking element that allows the cable 2864 to be pulled through the mechanism in a first direction when the release mechanism is engaged, but does not allow the cable 2864 to be pulled back through the release mechanism. When pressure is applied to the button of the respective release mechanisms 2882, 2884, the locking element will be disengaged and the cable 2864 may be pulled back through the pull tightening mechanisms 2874, 2876. In this manner, the tension in the stability straps 2832, 2838 can be quickly and easily adjusted by pulling the respective pull tabs 2878, 2880.

In an alternative configuration, the looped first ends 2834, 2840 of the stability straps 2832, 2838 can be permanently secured to the straps themselves, and adjustment of the straps can be provided solely via the pull tightening mechanisms 2874, 2876.

Turning now to the force strap 2844, the first and second ends 2846, 2848 of the force strap 2844 are respectively received within the first and second receiving portions 2852, 2854 arranged along the distal portion of the proximal shell 2812. As previously stated, the force strap 2844 is spirally wound around the leg and knee brace 2810, and passes through the force strap retainer 2850 formed along the proximal portion of the distal shell 2818. The force strap 2844 is utilized to provide desired stability and support, and/or unloading of the joint.

The first and second ends 2846, 2848 of the force strap 2844 are each respectively connected via an end connector 2858, 2860 to a respective cable 2864. Each of the respective cables 2864 is further connected to a dial tensioning mechanism 2862 that can be manipulated in a first direction to tension the force strap 2844 or a second direction to loosen the force strap 2844.

The first and second ends 2846, 2848 of the force strap 2844 are visible through slots in the receiving portions 2852,

2854. The indicia 2856 are arranged along the slots, such that the marker that corresponds to the position of the first and second ends 2846, 2848 of the force strap 2844 indicates the amount of tension in the force strap.

As can be seen, once a user positions their leg within the knee brace 2810, the stability and force straps can be quickly and easily adjusted to provide the proper amount of strap tension in order to achieve the desired amount of support and stabilization, and/or unloading of the joint. Thus, the knee brace 2810 can be easily adjusted by all users, and in particular the infirm and elderly In view of the above description, an exemplary embodiment of a lightweight, low cost, versatile and easily adjustable brace with quick strap tensioning is described.

S. Conclusion

The disclosed embodiments of orthopedic devices and particularly a circumferential walker provide many improvements and allow easy insertion or removal of the lower leg into the walker. Additionally, the tightening mechanisms allow quick and easy tightening of the walker around the lower leg in order to provide the necessary support and stabilization of the lower leg. Accordingly, the disclosed embodiments of a circumferential walker are easier to don and doff, which will be advantageous to numerous users, including the elderly or infirm.

While particular embodiments of orthopedic devices are discussed above utilizing certain parts and materials, the components of the devices described herein may be formed in any suitable manner recognized by a skilled artisan, such as casting, machining, stereolithography, or any other suitable process.

One of the disclosed embodiments of an orthopedic device provides an improved knee brace that is lightweight and low cost and has a lower profile than a typical brace, and provides quick strap tensioning such that all users can easily adjust the brace for proper fit, support, stabilization, and/or unloading of the joint.

It is understood that the size of the disclosed embodiments and the components thereof can be adjusted so that different users having different sized knees, legs, ankles, and feet may benefit from the present design. Specifically, the width, thickness and length of the shells and sole members may be varied to accommodate different sized users.

It is also understood that the locations of the various components and connection points can be alternated from those shown, such that the connection points may be altered from the positions as illustrated herein.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features from different embodiments. For example different connecting mechanisms may be freely changed and substituted. Additionally, any suitable tightening mechanism may be utilized, such as lacing or hook and loop strap fasteners. Further, each of the dorsal shell configurations may be applied to a posterior shell configuration and vice versa. In addition to the variations described herein, other known equivalents for each feature can be mixed and matched by one of ordinary skill in this art to construct a circumferential walker in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

We claim:

1. A circumferential walker comprising:
   at least one frame member including a posterior shell contoured to generally correspond to at least one of a lower leg, ankle, and foot of a user, wherein the posterior shell defines first and second side portions on opposed sides of an anterior opening formed by the posterior shell and bordered by at least one of lower leg, ankle, and foot sections of the posterior shell, the at least one frame member further including a dorsal shell contoured to correspond to a dorsal aspect of at least one of a lower leg, ankle, and foot of a user;
   a strapping system including a dial tensioning device and at least one cable having a first end connected to the dial tensioning device and a second end securable to at least one strap, the dial tensioning device comprising a rotary ratchet permitting incremental adjustment of a length of the at least one cable connecting to the at least one strap, the at least one strap fixed to the first side portion of the at least one frame member and extends over the dorsal shell, and the dial tensioning device detachably secured to the second side portion of the at least one frame member;
   wherein adjustment of the dial tensioning device in a first direction urges the first and second side portions of the posterior shell to bend about an anatomical limb and/or secures the posterior shell to the limb, and draws the dorsal shell toward the opening of the posterior shell by tensioning the at least one strap over the dorsal shell;
   wherein the at least one cable comprises a main cable portion connected to at least one strap cable, the at least one strap cable corresponding and connecting to the at least one strap;
   wherein the at least one cable attaching to the dial tensioning device at the main cable portion;
   wherein the at least one strap cable comprises a plurality of strap cables connecting to a plurality of straps, the plurality of strap cables attaching to the main cable portion at a single connection point.

2. The circumferential walker of claim 1, wherein adjustment of the dial tensioning device in a first direction urges both of the posterior and dorsal shells against the user and/or secures both of the posterior and dorsal shells to the limb.

3. The circumferential walker of claim 2, wherein the dorsal shell is flexible and arranged to bend upon actuation of the dial tensioning device.

4. The circumferential walker of claim 3, wherein the dorsal shell bends about the first and second side portions of the posterior shell as the dial tensioning device is adjusted in the first direction.

5. The circumferential walker of claim 1, wherein the posterior shell is flexible and is arranged to bend upon actuation of the dial tensioning device.

6. The circumferential walker of claim 1, wherein adjustment of the dial tensioning device in a first direction places the dorsal shell against the first and second side portions of the posterior shell and closes the anterior opening.

7. The circumferential walker of claim 1, wherein the dorsal shell is wider than the anterior opening.

8. The circumferential walker of claim 1, wherein the dorsal shell has a width overlapping the first and second side portions of the posterior shell.

* * * * *